US009133233B2

(12) United States Patent
Gryaznov et al.

(10) Patent No.: US 9,133,233 B2
(45) Date of Patent: Sep. 15, 2015

(54) RNA AMIDATES AND THIOAMIDATES FOR RNAI

(75) Inventors: Sergei Gryaznov, San Mateo, CA (US); Krisztina Pongracz, Oakland, CA (US)

(73) Assignee: Geron Corporation, Menlo Park, CA (US)

( * ) Notice: Subject to any disclaimer, the term of this patent is extended or adjusted under 35 U.S.C. 154(b) by 1207 days.

(21) Appl. No.: 10/578,530

(22) PCT Filed: Nov. 3, 2004

(86) PCT No.: PCT/US2004/032780
§ 371 (c)(1),
(2), (4) Date: Feb. 1, 2007

(87) PCT Pub. No.: WO2005/047506
PCT Pub. Date: May 26, 2005

(65) Prior Publication Data
US 2007/0275919 A1    Nov. 29, 2007

Related U.S. Application Data

(60) Provisional application No. 60/516,769, filed on Nov. 4, 2003.

(51) Int. Cl.
C12N 15/11 (2006.01)
C07H 21/00 (2006.01)

(52) U.S. Cl.
CPC .............. *C07H 21/00* (2013.01); *C12N 15/111* (2013.01); *C12N 2310/14* (2013.01); *C12N 2310/3145* (2013.01); *C12N 2310/3515* (2013.01); *C12N 2320/51* (2013.01)

(58) Field of Classification Search
USPC ......... 435/6, 91.1, 91.31, 455, 6.11, 6.1, 458; 514/44, 81; 536/23.1, 24.5; 544/243, 544/244
See application file for complete search history.

(56) References Cited

U.S. PATENT DOCUMENTS

| 5,591,607 A | 1/1997 | Gryaznov et al. |
| 5,599,922 A | 2/1997 | Gryaznov et al. |
| 5,631,135 A | 5/1997 | Gryaznov et al. |
| 5,684,143 A | 11/1997 | Gryaznov et al. |
| 5,726,297 A | 3/1998 | Gryaznov et al. |
| 5,824,793 A | 10/1998 | Hirschbein et al. |
| 5,837,835 A | 11/1998 | Gryaznov et al. |
| 5,859,233 A | 1/1999 | Hirschbein et al. |
| 5,965,720 A | 10/1999 | Gryaznov et al. |
| 6,169,170 B1 | 1/2001 | Gryaznov et al. |
| 6,608,036 B1 | 8/2003 | Gryaznov et al. |
| 6,835,826 B2 | 12/2004 | Gryaznov et al. |
| 7,138,383 B2 | 11/2006 | Gryaznov et al. |
| 7,485,717 B2 | 2/2009 | Gryaznov et al. |
| 7,494,982 B2 * | 2/2009 | Gryaznov et al. ........... 514/44 R |
| 2002/0086356 A1 | 7/2002 | Tuschl et al. |
| 2002/0114784 A1 | 8/2002 | Li et al. |
| 2002/0162126 A1 | 10/2002 | Beach et al. |
| 2003/0027783 A1 | 2/2003 | Zernicka-Goetz et al. |
| 2004/0019003 A1 * | 1/2004 | Walter et al. ................ 514/44 |
| 2004/0053875 A1 | 3/2004 | Kreutzer et al. |
| 2005/0113325 A1 * | 5/2005 | Gryaznov et al. ........... 514/44 |
| 2005/0136430 A1 * | 6/2005 | Davis ................................ 435/6 |
| 2005/0164235 A1 * | 7/2005 | Manoharan et al. ............. 435/6 |
| 2005/0203044 A1 * | 9/2005 | Zinnen ........................... 514/44 |
| 2005/0244380 A1 * | 11/2005 | Krieg et al. .................. 424/93.2 |
| 2006/0116331 A1 * | 6/2006 | Jiang et al. ..................... 514/25 |
| 2006/0275769 A1 * | 12/2006 | Moses et al. ....................... 435/6 |
| 2006/0293262 A1 * | 12/2006 | Lieberman et al. ............. 514/44 |
| 2007/0037770 A1 | 2/2007 | Gryaznov et al. |
| 2008/0219968 A1 * | 9/2008 | Jaitner et al. ............... 424/130.1 |
| 2009/0149408 A1 | 6/2009 | McSwiggen et al. |
| 2014/0349292 A1 | 11/2014 | Gryaznov et al. |

FOREIGN PATENT DOCUMENTS

| AU | 2004220556 | 9/2004 |
| AU | 2004271215 | 3/2005 |
| AU | 2004320900 | 1/2006 |
| CA | 2522637 | 11/2004 |
| WO | 95/25814 | 9/1995 |
| WO | 97/31009 | 8/1997 |
| WO | 01/18015 | 3/2001 |
| WO | WO03100017 | * 5/2003 |
| WO | WO 03/100017 | * 12/2003 |
| WO | WO 2005/044976 | * 6/2004 |
| WO | WO 2004/080406 | 9/2004 |
| WO | 2006/014387 | 2/2006 |

OTHER PUBLICATIONS

Pruzan et al., Nucleic acids REs., vol. 30, No. 2, pp. 559-568 (2002).*
International Search Report from PCT/US04/032780 Published as WO05/047506 A1.
Bertrand et al., "The Expression Cassette Determines the Functional Activity of Ribozymes in Mammalian Cells by Controlling Their Intracellular Localization", *RNA*, 3:75-88 (1997).
Elbashir et al., "Functional anatomy of siRNAs for mediating efficient RNAi in Drosophila melanogaster embryo lysate", *Embo Journal*, 20(23):6877-6888 (2001).
Good et al., "Expression of Small, Therapeutcis RNAs in Human Cell Nuclei", *Gene Therapy*, 4:45-54 (1997).
Gryaznov S M: "Oligonucleotide N3'->P5' phosphoramidates as potential therapeutic agents" *Biochimica et Biophysica ACTA*, 1489(1):131-140 (1999).
Matray et al., *Nucleic Acids Research*, 27(20):3976-3985 (1999).

(Continued)

*Primary Examiner* — Jane Zara
(74) *Attorney, Agent, or Firm* — Leslie A. Mooi

(57) ABSTRACT

The present disclosure relates to RNA amidates and thioamidates useful for RNA interference applications. The RNA amidates and thioamidates contain at least one internucleoside linkage chosen from ribo-N3'→P5' phosphoramidate (NP) and ribo-N3'→P5' thiophosphoramidate (NPS) linkages, and optionally further containing at least one covalently conjugated lipid moiety. Compositions comprising the amidates and thioamidates are disclosed, as are methods for their use in modulating gene expression.

17 Claims, 12 Drawing Sheets

(56) References Cited

OTHER PUBLICATIONS

McCaffrey et al., "*RNA Interference in Adult Mice*", *Nature*, 418:38-39 (2002).
Wianny et al., "Specific Interference with gene Function by Double-Stranded RNA in Early Mouse Development", *Nature Cell Biology*, 2:70-75 (1999).
Avino et al., *Bioorganic & Medicinal Chemistry*, 4(10):1649-1658 (1996).
Habus et al., *Bioconjugate Chemistry*, 9:283-291 (1998).
Nelson et al., *Nucleic Acids Research*, 20(23):6253-6259 (1992).
Rump et al., *Bioconjugate Chemistry*, 9:341-349 (1998).
Shea et al., *Nucleic Acids Research*, 18(13):3777-3783 (1990).
Stetsenko, D.A. and Gait, M.J., *Bioconjugate Chemistry*, 12:576-586 (2001).
Agami, R., "RNAi and related mechanisms and their potential use for therapy", *Curr. Op. Chem. Biol.* 6(6) (2002), pp. 829-834.
Holen, T., "Positional effects of short interfering RNAs targeting the human coagulation trigger Tissue Factor," Nucl. Acids Res. 30(8):1757-66 (2002).
Manoharan, M., "Oligonucleotide conjugates as potential antisense drugs with improved uptake, biodistribution, targeted delivery, and mechanism of action", Antisense & Nucl. Acid Drug Dev. 12, 2002, pp. 103-128.

\* cited by examiner

FIG. 1
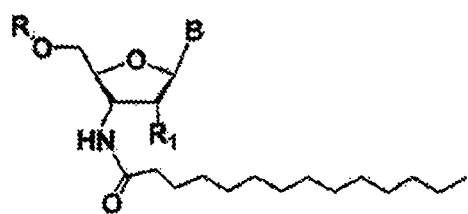
FIG. 1A
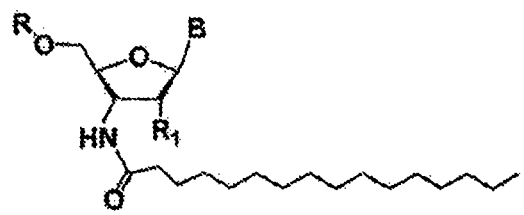
FIG. 1B
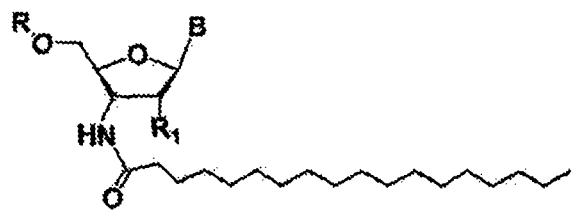
FIG. 1C
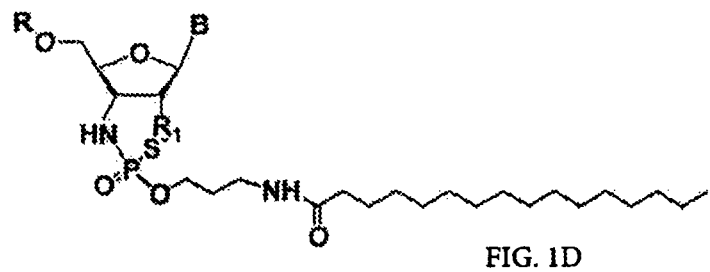
FIG. 1D

FIGURE 5
FIG. 5A
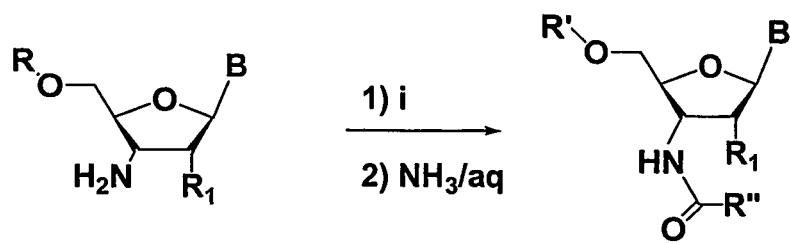
FIG. 5B
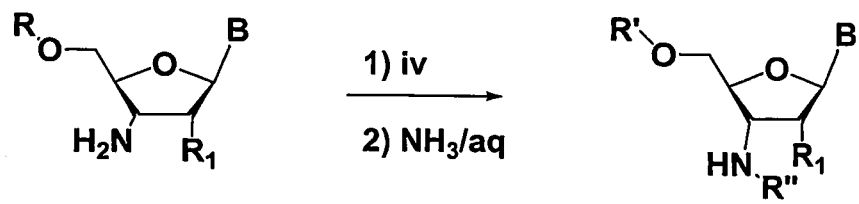

RNA AMIDATES AND THIOAMIDATES FOR RNAI

REFERENCE TO RELATED APPLICATIONS

This application is a 371 of International Application No. PCT/US04/032780 filed Nov. 3, 2004, which claims the priority benefit of U.S. Provisional Application No. 60/516,769 filed Nov. 4, 2003.

DESCRIPTION OF THE INVENTION

1. Field of the Invention

The present invention relates to the use of N3'→P5' phosphoramidate (NP) and N3'→P5' thiophosphoramidate (NPS) oligonucleotide chemistry for RNA interference, optionally including the addition of covalently linked lipid groups. N3'→P5' NP and N3'→P5' NPS chemistry confers superior stability characteristics on the molecules, and the optional addition of lipid groups confers superior cellular uptake.

2. Background of the Invention

Several kinds of potential nucleic acid therapeutics have been explored over the last two decades, including RNA inhibitors such as antisense, ribozymes (catalytic RNAs), and artificial ligand inhibitors ("aptamers"). These therapeutics are designed to silence gene expression, and thus to alleviate the effects of undesirable genes, be they endogenous to an organism or exogenous, such as bacterial or viral in origin. Because it is difficult to apply these to cells externally, there has been significant interest in expressing them within cells. However, expression of these therapeutics intracellularly has proved quite difficult as well; this difficulty is thought to be due to several factors. These include, for RNA-based therapeutics as an example, the considerations of finding their targets, folding into the effective configuration, and possibly interacting with the appropriate proteins while avoiding interactions with inappropriate proteins. There have been isolated promising results (see, for example, Bertrand, E. et al., *RNA* 3: 75-88 (1997); Good, P D et al. Gene Therapy 4:45-54 (1997)), but no therapeutics have yet resulted.

RNA Interference

RNA interference, or RNAi, is an endogenous, efficient, and potent gene-specific silencing technique that uses double-stranded RNAs (dsRNA) to mark a particular transcript for degradation in vivo. First discovered in the nematode *Caenorhabditis elegans*, it has since been found to operate in a wide variety of organisms. RNAi is believed to be effected by dsRNAs ~21-25 nucleotides long, called short interfering RNAs (siRNAs), which are endogenously produced through the degradation of long dsRNA molecules by an RNAse III-related nuclease called Dicer. Once formed, the siRNAs associate with a multiprotein complex called RISC (RNA-Induced Silencing Complex), which targets the homologous RNA by Watson-Crick base pairing for sequence specific degradation of mRNA.

This sequence-specific degradation of mRNA results in knocking down (partially or completely) the targeted gene. Thus RNAi provides an alternative to presently available methods of knocking down (or out) a gene or genes. This method of knocking down gene expression can be used therapeutically or for research (e.g., to generate models of disease states, to examine the function of a gene, to assess whether an agent acts on a gene, or to validate targets for drug discovery).

There are two main approaches to employing RNAi in cells. In the first approach, an expression construct (for either integrative or transient expression), which encodes an RNA including the desired RNAi sequences, is introduced into the target cells. The endogenous dicer enzyme recognizes and processes this RNA into the desired ~21-23 nucleotide siRNAs, which then enter an effector complex, RISC. In the second approach, the siRNAs (in either single-stranded antisense or double-stranded form) are introduced directly into the cell and directly enter the RISC complex. In both of these approaches, guided by the antisense strand of the siRNA, the active form of RISC (activated by the ATP-dependent unwinding of the siRNA duplex) recognizes and suppresses gene expression through mRNA degradation or prevention of protein synthesis.

RNAi has been studied in a variety of systems. Fire et al., *Nature*, 391: 806 (1998), were the first to observe RNAi in *C. elegans*. Wianny and Goetz, *Nature Cell Biol.*, 2:70 (1999), describe RNAi mediated by dsRNA in mouse embryos. Hammond et al., Nature, 404:293 (2000), describe RNAi in *Drosophilia* cells transfected with dsRNA. Elbashir et al., *Nature*, 411:494 (2001), describe RNAi induced by introduction of duplexes of synthetic 21-nucleotide RNAs in cultured mammalian cells by including human duplexes of synthetic 21-nucleotide RNAs in cultured mammalian cells including embryonic kidney and HeLa cells.

Recent work in *Drosophilia* embryonic lysates (Elbashir et al., *EMBO J.*, 20:6877(2001)) has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs. Furthermore, complete disubstitution of one or both siRNA strands with 2'deoxy (2'-H) or 2'-O-methyl nucleotides abolishes RNAi activity, whereas substitution of the 3'-terminal siRNA overhang nucleotides with 2'deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., *EMBO J.*, 20:6877 (2001)). Other studies have indicated that a 5'-phosphate on the target complementary strand of a siRNA duplex is required for siRNA activity and that ATP is utilized to maintain the 5'-phosphate moiety on the siRNA (Nykanen et al., *Cell*, 107:309 (2001)).

Studies have shown that replacing the 3'-terminal nucleotide overhanging segments of a 21-mer siRNA duplex having two-nucleotide 3'-overhangs with deoxyribonucleotides does not have an adverse effect on RNAi activity. Replacing up to 4 nucleotides on each end of the siRNA with deoxyribonucleotides has been reported to be well-tolerated, whereas complete substitution with deoxyribonucleotides results in no RNAi activity. In addition, Elbashir et al., supra, also report that substitution of siRNA with 2'-O-methyl nucleotides completely abolishes RNAi activity. Li et al., International PCT Publication No. WO 00/44914, and Beach et al., International PCT Application No. WO 01/68836 preliminarily suggest that siRNA may include modifications to either the phosphate sugar backbone or the nucleoside to include at least one of a nitrogen or sulfur heteroatom; however, neither application postulates to what extent such modifications would be tolerated in siRNA molecules, nor provides any further guidance or examples of such modified siRNA. Kreutzer et al., Canadian Patent Application No. 2,359,180, also describe certain chemical modifications for use in dsRNA constructs in order to counteract activation of double stranded RNA-dependent protein kinase PKR, specifically 2'-amino or 2'-O-methyl nucleotides, and nucleotides containing a 2'-O or 4'-C methylene bridge. However, it is unclear as to what extent these modifications would be tolerated in siRNA molecules.

The use of longer dsRNA has been described. For example, Beach et al., International PCT Publication No. WO 01/68836, describes specific methods for attenuating gene expression using endogenously-derived dsRNA. Tuschl et. al. International PCT Publication No. WO 01/75164, describe a *Drosophilia* in vitro RNAi system and the use of specific siRNA molecules for certain functional genomic and certain therapeutic applications; although Tuschl, *Chem. Biochem.*, 2:239-245 (2001), doubts that RNAi can be used to cure genetic diseases or viral infection due to the danger of activating interferon response. Li et. al., International PCT Publication No. 01/36646, describe certain methods for inhibiting the expression of particular genes in mammalian cells using dsRNA molecules. Fire et al., International PCT Publication No. WO 99/32619, describe particular methods for introducing certain dsRNA molecules into cells for use in inhibiting gene expression. Plaetinck et al., International PCT Publication No. WO 00/01846, describe certain methods for identifying specific genes responsible for conferring a particular phenotype in a cell using specific dsRNA molecules. Mello et al., International PCT Publication No. WO 01/29058, describe the identification of specific genes involved in dsRNA-mediated RNAi. Deschamps Depaillette et al., International PCT Publication No. WO 99/07409, describe specific compositions consisting of particular dsRNA molecules combined with certain anti-viral agents. Waterhouse et al., International PCT Publication No. 99/53050, describe certain methods for decreasing the phenotypic expression of a nucleic acid in plant cells using certain dsRNAs. Driscoll et al., International PCT Publication No. WO 01/49844, describe specific DNA constructs for use in facilitating gene silencing in targeted organisms.

Others have reported on various RNAi and gene-silencing systems. For example, Parrish et al., *Molecular Cell*, 6: 1977-1087 (2000), describe chemically modified siRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/38551, describe certain methods for modifying genetic characteristics of an organism using certain dsRNAs. Cogoni et al., International PCT Publication No. WO 01/53745, describe certain methods for isolating a neurospora silencing gene and uses thereof. Reed et al., International PCT Publication No. WO 01/70944, describe certain methods of drug screening using transgenic nematodes as Parkinson's Disease models using certain dsRNAs. Deak et al., International PCT Publication No. WO 01/72774, describe certain *Drosophilia*-derived gene products that may be related to RNAi in *Drosophilia*. Arndt et al., International PCT Publication No. WO 01/92513 describe certain methods for mediating gene suppression by using factors that enhance RNAi. Tuschl et al., International PCT Publication No. WO 02/44321, describe certain synthetic siRNA constructs. Pachuk et al., International PCT Publication No. WO 00/6334, and Satishchandran et al., International PCT Publication No. WO 01/04313, describe certain methods and compositions for inhibiting the function of certain polynucleotide sequences using certain dsRNAs. Echeverri et al., International PCT Publication No. WO 02.38805, describe *C. elegans* genes identified via RNAi. Kruetzer et al., International PCT Publications Nos. WO 02/055692, WO 02/055693, and EP 1144623 B1 describe certain methods for inhibiting gene expression using RNAi. Graham et al., International PCT Publication Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (greater than 25 nucleotide) constructs that mediate RNAi.

Delivering siRNAs directly to whole vertebrate animals is more problematic than it is for invertebrates or cell lines. Conventionally constructed oligonucleotides have poor serum stability, are susceptible to nuclease degradation, and cannot easily cross cell membranes. Two groups of scientists independently employed a "hydrodynamic transfection method" to deliver naked siRNAs to mice via tail-vein injection. A. P. McCaffrey et al., "Gene expression: RNA interference in adult mice," *Nature*, 418:38-9 (2002); D. J. Lewis et al., "Efficient delivery of siRNA for inhibition of gene expression in postnatal mice," *Nat. Genet.*, 32:107-8 (2002). While these scientists observed downregulation of a reporter gene by 80%-90% in the liver, kidney, spleen, lung, and pancreas, the effect was relatively short-lived, lasting only a few days.

Thus, there is a need to produce siRNAs that have improved characteristics for both in vitro delivery to cells and in particular, in vivo delivery for therapeutic applications.

The design of nucleic acids, particularly oligonucleotides, for in vivo delivery requires consideration of various factors including binding strength, target specificity, serum stability, resistance to nucleases and cellular uptake. A number of approaches have been proposed in order to produce oligonucleotides that have characteristics suitable for in vivo use, such as modified backbone chemistry, formulation in delivery vehicles and conjugation to various other moieties. Therapeutic oligonucleotides with characteristics suitable for systemic delivery would be particularly beneficial.

Oligonucleotides with modified chemical backbones are reviewed in Micklefield, Backbone modification of nucleic acids: synthesis, structure and therapeutic applications, *Curr. Med. Chem.*, 8(10):1157-79, 2001 and Lyer et al., Modified oligonucleotides—synthesis, properties and applications, *Curr. Opin. Mol. Ther.*, 1(3): 344-358, 1999.

Examples of modified backbone chemistries include:
peptide nucleic acids (PNAs) (see Nielsen, *Methods Mol. Biol.*, 208:3-26, 2002),
locked nucleic acids (LNAs) (see Petersen & Wengel, *Trends Biotechnol.*, 21(2):74-81, 2003),
phosphorothioates (see Eckstein, *Antisense Nucleic Acid Drug Dev.*, 10(2):117-21, 2000),
methylphosphonates (see Thiviyanathan et al., *Biochemistry*, 41(3):827-38, 2002),
phosphoramidates (see Gryaznov, *Biochem. Biophys. Acta*, 1489(1):131-40, 1999; Pruzan et al., *Nucleic Acids Res.*, 30(2):559-68, 2002), and
thiophosphoramidates (see Gryaznov et al., *Nucleosides Nucleotides Nucleic Acids*, 20(4-7):401-10, 2001; Herbert et al., *Oncogene*, 21(4):638-42, 2002).

Each of these types of oligonucleotides has reported advantages and disadvantages. For example, peptide nucleic acids (PNAs) display good nuclease resistance and binding strength, but have reduced cellular uptake in test cultures; phosphorothioates display good nuclease resistance and solubility, but are typically synthesized as P-chiral mixtures and display several sequence-non-specific biological effects; methylphosphonates display good nuclease resistance and cellular uptake, but are also typically synthesized as P-chiral mixtures and have reduced duplex stability. The N3'→P5' phosphoramidate internucleoside linkages are reported to display favorable binding properties, nuclease resistance, and solubility (Gryaznov and Letsinger, *Nucleic Acids Research*, 20:3403-3409, 1992; Chen et al., *Nucleic Acids Research*, 23:2661-2668, 1995; Gryaznov et al., *Proc. Natl. Acad. Sci.*, 92:5798-5802, 1995; Skorski et al., *Proc. Natl. Acad. Sci.*, 94:3966-3971, 1997). However, they also show increased acid lability relative to the natural phosphodiester counterparts (Gryaznov et al., *Nucleic Acids Research*, 24:1508-1514, 1996). Acid stability of an oligonucleotide is an important quality given the desire to use oligonucleotide agents as oral therapeutics. The addition of a sulfur atom to the backbone in N3'→P5' thiophosphoramidate oligonucleotides provides enhanced acid stability.

As with many other therapeutic compounds, the polyanionic nature of oligonucleotides reduces the ability of the compound to cross lipid membranes, limiting the efficiency of cellular uptake. Various solutions have been proposed for increasing the cellular uptake of therapeutic agents, including formulation in liposomes (for reviews, see Pedroso de Lima et al., *Curr. Med. Chem.*, 10(14):1221-1231, 2003 and Miller, *Curr. Med. Chem.*, 10(14):1195-211, 2003) and conjugation with a lipophilic moiety. Examples of the latter approach include: U.S. Pat. No. 5,411,947 (Method of converting a drug to an orally available form by covalently bonding a lipid to the drug); U.S. Pat. No. 6,448,392 (Lipid derivatives of antiviral nucleosides: liposomal incorporation and method of use); U.S. Pat. No. 5,420,330 (Lipo-phosphoramidites); U.S. Pat. No. 5,763,208 (Oligonucleotides and their analogs capable of passive cell membrane permeation); Gryaznov & Lloyd, *Nucleic Acids Research*, 21:5909-5915, 1993 (Cholesterol-conjugated oligonucleotides); U.S. Pat. No. 5,416,203 (Steroid modified oligonucleotides); WO 90/10448 (Covalent conjugates of lipid and oligonucleotide); Gerster et al., *Analytical Biochemistry*, 262:177-184 (1998) (Quantitative analysis of modified antisense oligonucleotides in biological fluids using cationic nanoparticles for solid-phase extraction); Bennett et al., *Mol. Pharmacol.*, 41:1023-1033 (1992) (Cationic lipids enhance cellular uptake and activity of phophorothioate antisense oligonucleotides); Manoharan et al., *Antisense and Nucleic Acid Drug Dev.*, 12:103-128 (2002) (Oligonucleotide conjugates as potential antisense drugs with improved uptake, biodistribution, targeted delivery and mechanism of action); and Fiedler et al., *Langenbeck's Arch. Surg.*, 383:269-275 (1998) (Growth inhibition of pancreatic tumor cells by modified antisense oligodeoxynucleotides).

SUMMARY OF THE INVENTION

This invention aids in fulfilling these needs in the art. In accordance with the invention, there is provided a small interfering RNA comprising 15-25 nucleotides complementary to a target nucleic acid sequence, wherein the RNA comprises at least one internucleoside linkage chosen from ribo-N3'→P5' phosphoramidate (NP) and ribo-N3'→P5' thiophosphoramidate (NPS) linkages.

According to another aspect of the invention, there is provided a compound comprising the structure O-(x-L)$_n$, wherein O is a riboamidate of formula:

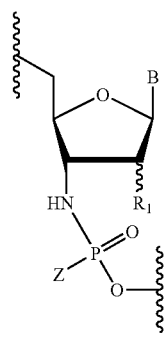

$R_1$ is chosen from fluorine and $OR_2$, $R_2$ is chosen from hydrogen and lower alkyl, B is chosen from purines, pyrimidines, and analogs thereof, and Z is chosen from oxygen and sulfur, and further wherein the riboamidate comprises a sequence of 15 to 25 bases, and said sequence is at least partially complementary to a selected target sequence; L is a lipid moiety; x is an optional linker; and n is an integer ranging from 1 to 5, wherein if n>1, each additional (x-L) component may be, independently, the same or different.

According to still another aspect of the invention, there is provided a method for effecting the post-transcriptional silencing of at least one gene, comprising administering to a mammal in need of such post-transcriptional silencing at least one a small interfering RNA comprising 15-25 nucleotides complementary to a target nucleic acid sequence, wherein the RNA comprises at least one internucleoside linkage chosen from ribo-N3'→P5' phosphoramidate (NP) and ribo-N3'→P5' thiophosphoramidate (NPS) linkages.

According to yet another aspect of the invention, there is provided a method for regulating the expression of genes in an organism, comprising administering to a mammal in need of such regulation at least one small interfering RNA comprising 15-25 nucleotides complementary to a target nucleic acid sequence, wherein the RNA comprises at least one internucleoside linkage chosen from ribo-N3'→P5' phosphoramidate (NP) and ribo-N3'→P5' thiophosphoramidate (NPS) linkages.

According to still a further aspect of the present invention, there is provided a single-stranded small interfering RNA that inhibits the expression of an endogenous mammalian target RNA sequence, wherein the single-stranded small interfering RNA comprises at least one internucleoside linkage chosen from ribo-N3'→P5' phosphoramidate (NP) and ribo-N3'→P5' thiophosphoramidate (NPS) linkages.

The compositions and methods of the present invention relate to RNA amidates and thioamidates, optionally comprising at least one covalently linked lipid group, for RNAi applications. The compounds of the invention have superior cellular uptake properties. This means an equivalent biological effect can be obtained using smaller amounts of oligonucleotide. When applied to the human therapeutic setting, this can translate to reduced toxicity risks and cost savings. The compounds of the invention knock-out gene expression by RNA interference, e.g., by mediating interference of mRNA.

The mRNA of any gene can be targeted for degradation using the methods of mediating interference of mRNA. For example, any cellular or viral mRNA can be targeted and, as a result, the encoded protein (e.g., an oncoprotein, a viral protein), expression will be diminished. In addition, the mRNA of any protein associated with, or causative of, a disease or undesirable condition can be targeted for degradation.

For example, the compounds disclosed herein can be designed and used to modulate or block: Hepatitis B virus (HBV) and Hepatitis C virus (HCV) protein expression, and can thus be used to treat diseases associated with HBV and HCV such as, for example, cirrhosis, liver failure, and hepatocellular carcinoma; Ras gene expression, such as K-Ras (associated with colon and pancreatic carcinomas), H-Ras (associated with leukemias), and/or N-Ras expression; HIV-1 and HER2 gene expression, the latter of which is associated with breast and ovarian cancers; expression of vascular endothelial growth factor and/or vascular endothelial growth factor receptors, such as VEGFR1 and/or VEGFR2, for the purpose of, e.g., preventing, treating, controlling disorders and conditions related to angiogenesis, including but not limited to cancer, tumor angiogenesis, or ocular indications, such as diabetic retinopathy, or age-related macular degeneration, proliferative diabetic retinopathy, hypoxia-induced angiogenisis, rheumatoid arthritis, psoriasis, wound healing, endometriosis, endometrial carcinoma, gynecologic bleeding disorders, irregular menstrual cycles, ovulation, premenstrual syndrome (PMS), and menopausal dysfunction; beta-secretase (BACE), PIN-1, presenillin-1 (PS-1) and presenillin-2 (PS-2) polypeptide and polynucleotide targets, associated with Alzheimer's disease; expression of NOGO and NOGO receptor genes, and the expression of genes encoding the IkB kinase IKK complex, for example IKK-alpha, IKK-beta, or IKK-gamma and/or a protein kinase PKR protein; expression of kinases which phosphorylate Cdc25 S216, such as Chk1 (checkpoint kinase 1) enzyme, Chk2 (Cds1) and C-Tak1; and expression of the T-cell co-stimulatory adapter protein GRID (Grb2-related with Insert Domain).

In an exemplary therapeutic application, a 19 to 23 nucleotide riboamidate, such as a 21 to 23 nucleotide riboamidate, is introduced into a mammal or mammalian cells, for example a human or human cells, in order to mediate RNA interference in the mammal or mammalian cells, such as to prevent or treat a disease or undesirable condition. In this method, a gene (or genes) that cause or contribute to the disease or undesirable condition is targeted and a riboamidate complementary to the mRNA of the gene targeted for degradation is introduced into the cell or organism. The cell or organism is maintained under conditions under which degradation of the corresponding mRNA occurs, thereby mediating RNA interference of the mRNA in the gene in the cell or organism.

Two forms of RNAi are provided, a single-stranded form and a double-stranded form. Single-stranded forms are antisense (complementary to the coding strand of the targeted message) and are typically at least 17 bases in length, up to 50 bases in length, more usually from about 19 to about 25 bases in length, for example, from 19 to 23 bases in length. These single-stranded forms are suitably constituted with 100% riboamidates (NP or NPS), but can include other linkage forms, such as phosphodiester, and can also include some DNA nucleobases such as, for example, uracil, thymine, adenine, guanine, cytosine, and analogs thereof. The optional linkage of one or more lipid moieties is suitably to the 3' amino terminus or 5' terminus, but can also be to a nucleobase.

Double-stranded forms contain the sense and antisense regions and have the same size constraints as the single-stranded forms. They can be blunt-ended, or can include a 3' overhang to increase resistance to endonucleases. 5' overhangs are also possible. The antisense strand is the effector moiety, and is suitably entirely composed of riboamidates, but can also include some other linkage forms, including DNA nucleobases. The sense strand is less critical and other chemistries, including DNA, can be suitably employed.

BRIEF DESCRIPTION OF THE DRAWINGS

This invention will be described with reference to the drawings in which:

In FIG. 1, $R_1$ is chosen from fluorine and $OR_2$, wherein $R_2$ is chosen from hydrogen and lower alkyl.

FIG. 5 shows schematics of exemplary synthesis procedures for the compounds of the invention.). In FIG. 5, the following abbreviations apply:
  i=Cl—C(O)—R"/(i-Pr)2NEt, or HO—C(O)—R"/C.A, or [C(O)—R"]2O/(i-Pr)2NEt
  iv=R"–HC=O+[H]
  R=5'-CPG-Supported P,N-Protected Oligonucleotide
  R'=Deprotected NP- or NPS-Oligonucleotide
  R"=lipid moiety, L (to which a linker may be conjugated, if desired, see R'" for an example of a conjugated amino glycerol linker)
  R'"=—O—CH2(CHOH)CH2-NHC(O)—R"
  X=O, S; Y=H, or C(O)—R", Z=O or NH
  $R_1$=F, $OR_2$, wherein $R_2$ is H or alkyl.

FIGS. 5A and 5B show synthesis procedures that can be used for the production of compounds in which the lipid moiety is conjugated to the 3' terminus of the oligonucleotide. The scheme shown in FIG. 5B is a reductive amination starting with a lipid aldehyde; this produces an amine linkage between the lipid group and the oligonucleotide (see Schematic B below), in contrast to the scheme shown in FIG. 5A where the starting materials are carboxylic acid, acid anhydride or acid chloride forms of a fatty acid, resulting in the formation of an amide linkage (see Schematic A below

DETAILED DESCRIPTION OF THE INVENTION

1. Definitions

Figure 1E:
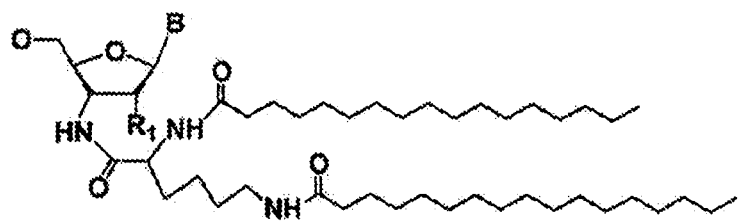
FIG. 1, comprising chemical structures 1A to 1DD, shows examples of the attachment of various lipid groups (L) to oligonucleotides in compounds of the invention.

An "alkyl group" refers to a straight, branched, or cyclic, substituted or unsubstituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$. The substituents can be chosen from, by way of non-limiting example, halogen, hydroxy, alkoxy, alkenyl, alkynyl, thio, nitro, amino, amide, acyl, and carboxyl.

An "acyl group" refers to a group having the structure RCO wherein R is an alkyl group. A lower acyl is an acyl wherein R is a lower alkyl group.

An "alkylamine" group refers to an alkyl group containing at least one attached nitrogen, and includes mono- and di-alkyl amines, e.g., 1-methyl-1-butylamine ($CH_3CHNH_2CH_2CH_2CH_3$), and the alkyl group can be further substituted with at least one substituent chosen from, by way of non-limiting example, halogen, hydroxy, alkoxy, alkenyl, alkynyl, thio, nitro, amino, amide, acyl, and carboxyl.

An "aryl group" refers to an aromatic ring group having 5-20 carbon atoms, such as phenyl, naphthyl, anthryl, or substituted aryl groups, such as, alkyl- or aryl-substitutions like tolyl, ethylphenyl, biphenylyl, etc. Also included are heterocyclic aromatic ring groups having 5-20 carbon atoms and at least one, for example 1-10, nitrogen, oxygen, and/or sulfur atoms in the ring.

"Oligonucleotide" refers to ribose and/or deoxyribose nucleoside subunit polymers having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→P5' thiophosphoramidate, and phosphorothioate linkages. Further, "oligonucleotides" includes modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage can be formed using the same chemistry or a mixture of linkage chemistries can be used. The term "polynucleotide", as used herein, has the same meaning as "oligonucleotide" and is used interchangeably with "oligonucleotide".

Whenever an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

As used herein, "nucleoside" includes the natural nucleosides, including 2'-deoxy and 2'-hydroxyl forms, e.g., as described in Komberg and Baker, DNA Replication, 2nd Ed. (Freeman, San Francisco, 1992), and analogs.

"Analogs" in reference to nucleosides includes synthetic nucleosides having modified nucleobase moieties (see definition of "nucleobase" below) and/or modified sugar moieties, e.g., described generally by Scheit, Nucleotide Analogs (John Wiley, New York, 1980). Such analogs include synthetic nucleosides designed to enhance binding properties, e.g., stability, specificity, or the like, such as disclosed by Uhlmann and Peyman (Chemical Reviews, 90:543-584, 1990).

The term "lipid" is used broadly herein to encompass substances that are soluble in organic solvents, but sparingly soluble, if at all, in water. The term lipid includes, but is not limited to, hydrocarbons, oils, fats (such as fatty acids, glycerides), sterols, steroids, and derivative forms of these compounds. Suitable lipids include fatty acids and their derivatives, hydrocarbons and their derivatives, and sterols, such as cholesterol. As used herein, the term lipid also includes amphipathic compounds, which contain both lipid and hydrophilic moieties.

Fatty acids usually contain even numbers of carbon atoms in a straight chain (commonly 12-24 carbons) and can be saturated or unsaturated, and can contain, or be modified to contain, a variety of substituent groups. For simplicity, the term "fatty acid" also encompasses fatty acid derivatives, such as fatty amides produced by the synthesis scheme shown in FIG. 5A (see for example, the compounds shown FIGS. 1A-1E).

The term "hydrocarbon" as used herein encompasses compounds that consist only of hydrogen and carbon, joined by covalent bonds. The term encompasses open chain (aliphatic) hydrocarbons, including straight chain and branched hydrocarbons, and saturated as well as mono- and polyunsaturated hydrocarbons. The term also encompasses hydrocarbons containing one or more aromatic rings.

The term "substituted" refers to a compound that has been modified by the exchange of one atom for another. In accordance with one aspect of the disclosure, the term is used in reference to halogenated hydrocarbons and fatty acids, including those in which one or more hydrogen atoms are substituted with fluorine.

A "nucleobase" as used herein includes (i) typical DNA and RNA nucleobases (uracil, thymine, adenine, guanine, and cytosine), (ii) modified nucleobases or nucleobase analogs (e.g., 5-methyl-cytosine, 5-bromouracil, or inosine), and (iii) nucleobase analogs. A nucleobase analog is a chemical whose molecular structure mimics that of a typical DNA or RNA base.

As used herein, "pyrimidine" means the pyrimidines occurring in natural nucleosides, including cytosine, thymine, and uracil, and analogs thereof, such as those containing substituents chosen from, for example, oxy, methyl, propynyl, methoxy, hydroxyl, amino, thio, and halo. The term as used herein further includes pyrimidines with protection groups attached, such as $N_4$-benzoylcytosine. Further pyrimidine protection groups are disclosed by Beaucage and Iyer (*Tetrahedron* 48:223-2311, 1992).

As used herein, "purine" means the purines occurring in natural nucleosides, including adenine, guanine, and hypoxanthine, and analogs thereof, such as those containing substituents chosen from, for example, oxy, methyl, propynyl, methoxy, hydroxyl, amino, thio, and halo. The term as used herein further includes purines with protection groups attached, such as $N_2$-benzoylguanine, $N_2$-isobutyrylguanine, $N_6$-benzoyladenine, and the like. Further purine protection groups are disclosed by Beaucage and Iyer (cited above).

As used herein, the term "protected" as a component of a chemical name refers to art-recognized protection groups for a particular moiety of a compound, e.g., "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups include those described in the following references: Gait, editor, *Oligonucleotide Synthesis: A Practical Approach* (IRL Press, Oxford, 1984); Amarnath and Broom, *Chemical Reviews*, 77:183-217, 1977; Pon et al., *Biotechniques*, 6:768-775, 1988; Ohtsuka et al., *Nucleic Acids Research,* 10:6553-6570, 1982; Eckstein, editor, *Oligonucleotides and Analogues: A Practical Approach* (IRL Press, Oxford, 1991); Greene and Wuts, *Protective Groups in Organic Synthesis,* Second Edition, (John Wiley & Sons, New York, 1991); Narang, editor, *Synthesis and Applications of DNA and RNA* (Academic Press, New York, 1987); Beaucage and Iyer (cited above), and like references.

The term "halogen" or "halo" is used in its conventional sense to refer to a chloro, bromo, fluoro or iodo substituent. In the compounds described and claimed herein, halogen substituents are generally fluoro, bromo, or chloro, suitably fluoro or chloro.

2. Design of Riboamidate and Ribothioamidate siRNAs

The riboamidate and thioriboamidate siRNAs disclosed herein include those having the formula O-(x-L)$_n$, wherein O is a riboamidate, L is a lipid moiety, x is an optional linker, and n is an integer ranging from 1 to 5. The design of such siRNAs requires the selection of O, L, and the determination of the structural linkage(s) between O and L, which may involve the optional linker group x.

The oligonucleotide component O may be regarded as the "effectoer" component of the compound in that it is this component that effects RNA interference by binding to the complementary target nucleic acid sequence. Thus, the sequence of O is chosen such that it includes a region comprising nucleotides complementary to a target nucleic acid sequence of a gene.

The riboamidate and ribothioamidate siRNAs may be provided in single stranded and double stranded forms. Single stranded forms are antisense (complementary to the coding strand of the targeted message), and it is the antisense strand that is most important in the applications disclosed herein.

The choice of the type of inter-nucleoside linkages used in synthesizing the riboamidates and ribothioamidates may be made from any of the available oligonucleotide chemistries. For the design of the antisense strands of single stranded and double stranded siRNAs, the inter-nucleoside linkages will generally be comprised of linkages chosen from N3'→P5' phosphoramidate and N3'→P5' thiophosphoramidate linkages. For double-stranded designs, more flexibility is permitted in the chemistry for the sense strand of double-stranded siRNAs, so that the linkages may be chosen from, but not limited to, phosphodiester, phosphotriester, methylphosphonate, P3'→N5' phosphoramidate, N3'→P5' phosphoramidate, N3'→P5' thiophosphoramidate, and phosphorothioate linkages.

Thus, according one aspect of the present invention, the siRNAs disclosed herein contain at least one linkage chosen from N3'→P5' phosphoramidate, and N3'→P5' thiophosphoramidate linkages, which may be represented by the structure: 3'-[—NH—P(=O)(—XR)—O—]-5', wherein X is O or S and R is chosen from hydrogen, alkyl, and aryl; and pharmaceutically acceptable salts thereof. According to another aspect of the invention, the linkages of the siRNAs disclosed herein are comprised entirely of N3'→P5' phosphoramidate and/or N3'→P5' thiophosphoramidate linkages. According to yet another aspect of the invention, at least 60% of the total linkages of the siRNAs disclosed herein are comprised of N3'→P5' phosphoramidate and/or N3'→P5' thiophosphoramidate linkages. In accordance with another aspect of the invention, at least 70%, for example at least 80% of the total linkages of the siRNAs disclosed herein are N3'→P5' phosphoramidate and/or N3'→P5' thiophosphoramidate linkages.

According to one aspect of the invention herein, the nucleotides of the siRNAs are comprised entirely of RNA nucleosides. According to another aspect, the siRNAs are comprised of RNA and DNA nucleosides. Thus, the term siRNA as used herein is intended to encompass chimeric molecules in which, while the majority of the nucleotides are RNA, it is permissible for some of the nucleotides to be DNA. This is especially the case for the sense region of double-stranded siRNAs.

Where a lipid moiety is to be conjugated to the 3' terminus of the riboamidate and ribothioamidate siRNAs disclosed herein, the synthesis of the conjugate is greatly facilitated by the presence of a 3' amino group. Hence, and irrespective of the chemistry selected, the addition of a 3' amino group is advantageous. The siRNAs are typically at least 17 bases in length, up to 50 bases in length, more usually from about 19 to about 25 bases in length. The siRNAs disclosed herein comprise a sequence of nucleotides complementary to a target nucleic acid sequence. According to one aspect of the invention, the nucleotide sequence of the siRNA is exactly complementary to the target nucleic acid sequence. However, it is not always necessary that the full length of the sequence of the nucleotide component be exactly complementary to the target sequence, the sequence can include residues or regions that are not complementary to the target sequence. Thus, according to another aspect of the invention, the nucleotide sequence of the siRNA is less than exactly complementary to the target nucleic acid sequence. The degree of complementarity depends on a variety of factors, such as, for example, the constitution of the gene targeted for RNA interference.

3. Synthesis of Riboamidate and Ribiothioamidate siRNAs

According to one aspect of the present invention, the compounds are represented by the formula:

O-(x-L)$_n$, where O represents the amidate, x is an optional linker group, L represents the lipid moiety, and n is an integer from 1-5.

Generally, the riboamidates and ribothioamidates disclosed herein can be prepared by a process comprising:

1) providing a first 3'-amino protected nucleoside, which is optionally attached to a solid phase support;
2) deprotecting the protected 3'-amino group to form a free 3'-amino group;
3) reacting the free 3'-amino group with a protected phosphoamidite ribonucleoside monomer to form an internucleoside N3'→P5' phosphoramidate linkage; and
4) oxidizing (or sulfurizing) the internucleoside N3'→P5' phosphoramidite linkage to form a phosphoramidate (or thiophosphoramidate) linkage.

According to one aspect of the invention, the protected phosphoramidate ribonucleoside monomers are (2'-t-butyldimethysilyl)-3'-(monomethoxytrityl)-amino-5'-O-(cyanoethyl-N,N'-diisopropyl-amino)-phosphoramite nucleoside monomers. In addition, the method of synthesizing an oligoribonucleotide can further include capping the free 3' amino groups that fail to react with the protected phosphoramidite ribonucleoside monomer.

Also disclosed herein is a solid phase method of synthesizing oligonucleotide N3'→P5' thiophosphoramidates using a modification of the phosphoramidite transfer methodology of Gryaznov, *Tetrahedron Letters,* 7661-64 (1999). Suitable non-limiting examples of solid phase supports include glass, beads, silica, etc. The synthetic strategy employed 3'-NH-trityl-protected 3'-aminonucleoside 5'-O-cyanoethyl-N,N-diisopropylaminophosphoramidites that were made by the method described in detail below. Every synthetic cycle was conducted using the following chemical procedures: 1) detritylation, 2) coupling; 3) capping; and 4) sulfurization. For a step-wise sulfurization of the internucleaside phosphoramidite group formed after the coupling step, the iodine/water based oxidizing agent was replaced by the sulfurizing agents—either by elemental sulfur $S_8$ or by the commonly used Beaucage reagent—3H-1,2-benzodithiol-3-one 1,1 dioxide (Iyer et al., *J. Organic Chemistry* 55:4693-4699, 1990). The oligonucleotide syntheses were performed (1 μmole synthesis scale) with a 1% solution of Beaucage reagent in anhydrous acetonitrile or 15% $S_8$ in $CS_2/Et_3N$, 99/1 (vol/vol) as the sulfurizing agent.

Chimeric N3'→P5' phosphoramidate-phosphorthioamidate oligonucleotides can be made by using an oxidation step(s) after the coupling step, which results in formation of a phosphoramidate internucleoside group. Similarly, phosphodiester-phosphorthioamidates can be made by using 5'-phosphoramidite-3'-O-DMTr-protected nucleotides as monomeric building blocks.

Figure 2:
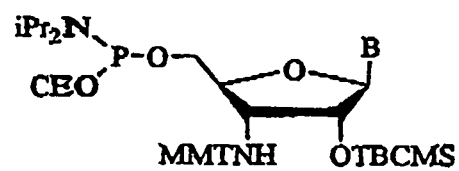
FIG. 2 shows the structure of the ribophosphoramidite monomers that are used to synthesize oligoribonucleotide N3'→P5' phosphoramidates where: B is cytosine, uracil, 2,6-diaminopurine, or guanine; MMTNH is (monomethoxytrityl) amino; OTBDMS is —O-t-butyldimethysilyl; $iPr_2N$ is diisopropylamino; and CEO is β-cyanoethyl. In addition, when B is cytosine, the N4 amino group of cytosine is protected with a benzoyl group; when B is 2,6-diaminopurine, the exocylic amine groups are protected with a phenoxyacetyl group, or when B is guanine the N2 amino group of guanine is protected with an isobutyl group.

Initial investigations into the assembly of oligoribonucleotide N3'→P5' phosphoramidates determined that a synthetic methodology based on a phosphoramidite transfer reaction was suitable for construction of these biopolymers (Gryaznov, et al. (1998) *Nucleic Acids Res.*, 26:4160-4167). This approach was previously employed for the synthesis of oligo-2'-fluoro-2'-deoxynucleotide N3'→P5' phosphoramidates as well as for oligo-2'-deoxynucleotide N3'→P5' phosphoramidates (Schultz, et al. (1996) *Nucleic Acids Res.*, 24, 2966-2973; McCurdy, et al. (1997) *Tetrahedron Lett.*, 38, 207-210; Nelson, et al. (1997) *J. Org. Chem.*, 62, 7278-7287). The synthetic strategy employed in accordance with the present invention is based on the use of 3'-(monomethoxytrityl)amino-5'-O-(cyanoethyl-N,N'-diisopropylamino)-phosphoramidite nucleoside monomers (FIG. 2) and assembly of the oligoribonucleotide in the 5' to 3' direction. The appropriately protected ribonucleotide monomers were in general synthesized according to the previously reported protocols (Gryaznov, et al. (1998) *Nucleic Acids Res.*, 26:41 604-167), which were modified thereby allowing for maximization of overall yields and expediting isolation of the final products (FIG. 3).

Disclosed herein is a synthetic method for the preparation of the monomers, resulting in the rapid access to the final products with improved overall yields. In general, the 2' position is selectively deprotected; the azido group at the 3' position is reduced to an amine; the 2' and 3' position are then protected, suitably with each position having a different protecting group such that each position can be selectively deprotected; the 5' protecting group is selectively deprotected; and the 5'-OH group is phosphitylated to provide the monomers of FIG. 2 that are the phosphoramide building blocks.

The selective removal of the protecting group at the 2' position and the reduction of the azido group at the 3' position can be done sequentially or concurrently if the protecting group is chosen such that it can be removed under the reduction conditions. Thus, if the 2' position is protected with a benzyl group, and the reduction is done under the appropriate conditions, the removal of the benzyl group and the reduction of the azido group can be accomplished in one step. Generally, the 2' position is deprotected to prevent the commonly used 2' protecting groups, such as acetyl and benzoyl, from migrating to the 3' amino position. Thus, according to one aspect of the invention, the protecting group at the 2' position is chosen such that it does not migrate to the 3' position and therefore does not need to be removed before reduction of the azido group.

Figure 3:
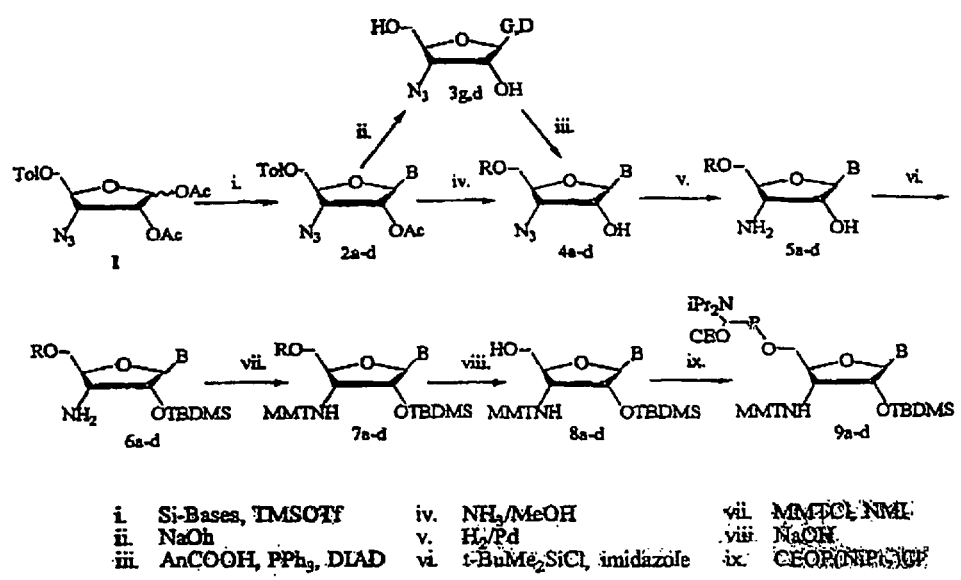
FIG. 3 shows the overall synthetic scheme used to prepare most of the protected ribophosphoramidite monomers of the present invention. B represents a base selected from the group consisting of adenine (A), guanine (G), 2,6-diaminopurine (D), uracil (U), cytosine (C) and thymidine (T). Tol is toluoyl, MMTNH is (monomethoxytrityl)amino, OTBDMS is —O-t-butyidimethysilyl, $iPr_2N$ is diisopropylamino, and CEO is β-cyanoethyl, R is anisoyl when the base is G or D, and toluoyl when the base is A, T, or U. In addition, when B is adenine, the N6 amino group of adenine is protected with a benzoyl group; when B is 2,6-diaminopurine, the exocylic amine groups are protected with a phenoxyacetyl group; or when B is guanine the N2 amino group of guanine is protected with an isobutyl group.

As depicted in FIG. 3, the first step of the synthesis involved tin(IV) chloride or trimethylsilyl triflate mediated glycosylation of trimethylsilylated nucleobases (Azhayev, et al. (1979) *Nucleic Acids Res.*, 2:2625-2643; Vorbruggen, et al. (1981) *Chem. Ber.*, 114:1234-1255) to a commonly employed sugar precursor 3-azido-1,2-di-O-acetyl-5-O-toluoyl-3-deoxy-D-ribofuranose 1, which was prepared according to literature procedure (Ozols, et al. *Synthesis*, 557-558). Adenine was protected at $N^6$ with a benzoyl group, while guanine was blocked at $N^2$ with an isobutyl group and at $O^6$ with diphenylcarbamate (Zou, et al. (1987) *Can. J. Chem.*, 65:1436-1437). The protection of $O^6$ with this bulky group allows for selective glycosylation to occur at $N^9$ with very little (≤10%) formation of the undesired $N^7$ regioisomer as judged by TLC analysis. 2,6-Diaminopurine was protected at each exocylic amine with a phenoxyacetyl group for all glycosylation reactions with this highly polar purine base analogue (Schulhof, et al. (1987) *Tetrahedron Lett.*, 28:51-54).

Then experimental conditions were found, which provided for the selective removal of the 2'-O-protecting group, such as acetyl, benzyl, benzoyl, or trialkylsilyl, in the presence of the 5'-O-protecting group, such as toluoyl or benzoyl (Neilson, et al. (1971) *Can. J. Chem.*, 49:493-498) (FIG. 3). This allowed for the omission of a 5'-hydroxyl reprotection step from the synthetic protocol. Also, a low yielding series of steps late in the monomer synthesis, used in the literature procedure (Gryaznov, et al. (1998) *Nucleic Acids Res.*, 26:4160-4167) to convert a 5'-O-trityl-nucleoside precursor to the 3'-N-tritylprotected amino intermediate, were also avoided.

Following the glycosylation reaction, the next five chemical transformations resulted in very high yields of the products. This eliminated the need for intermediate purification after the chemical conversions of iv-viii. (FIG. 3), thus providing a rapid and convenient access to compounds of structure 8. However, it should be noted that for the guanosine and 2,6-diaminopurine analogues, selective removal of the 2'-O-acetyl protecting group was unsuccessful. Thus, both 2'-O- and 5'-O-protecting groups were removed, after which the 5'-hydroxyl group was selectively reprotected (FIG. 3(*iii*)).

For compound 2 (FIG. 3), where the base (B) was A, T, or U, the 2'-O-acetyl group was selectively removed using a base, optionally in an hydrophilic organic solvent followed by the reduction of the 3'-azido group to an amine group.

Appropriate solvents are those which will at least partially dissolve one or all of the reactants and will not adversely interact with either the reactants or the product. Non-limiting examples of suitable solvents include aromatic hydrocarbons such as toluene, o-, m- and p-xylene, halogenated hydrocarbons, such as methylene chloride, chloroform and chlorobenzene, ethers such as diethyl ether, diisopropyl ether, tert-butyl methyl ether, dioxane, anisole, and tetrahydrofuran, nitriles, such as acetonitrile and propionitrile, ketones, such as acetone, methyl ethyl ketone, diethyl ketone, and tert-butyl methyl ketone, alcohols such as methanol, ethanol, n-propanol, isopropanol, n-butanol and tert-butanol, and also dimethyl sulfoxide (DMSO), dimethylformamide (DMF), and water. According to one aspect, the suitable solvents are chosen from DMSO, DMF, acetonitrile, and toluene. Mixtures of solvents can also be used.

Non-limiting examples of suitable bases include, generally, inorganic compounds, such as alkali metal hydroxides and alkaline earth metal hydroxides, such as lithium hydroxide, sodium hydroxide, potassium hydroxide, and calcium hydroxide, alkali metal oxides and alkaline earth metal oxides, such as lithium oxide, sodium oxide, calcium oxide, and magnesium oxide, alkali metal hydrides and alkaline earth metal hydrides, such as lithium hydride, sodium hydride, potassium hydride and calcium hydride, alkali metal amides, such as lithium amide, sodium amide, and potassium amide, alkali metal carbonates and alkaline earth metal carbonates, such as lithium carbonate and calcium carbonate, and also alkali metal hydrogen carbonates such as sodium hydrogen carbonate, organometal compounds, in particular alkali metal alkyls, such as methyllithium, butyllithium, and phenyllithium, alkylmagnesium halides, such as methylmagnesium chloride, and alkali metal alkoxides and alkaline earth metal alkoxides, such as sodium methoxide, sodium ethoxide, potassium ethoxide, potassium tert-butoxide, and dimethoxymagnesium, furthermore organic bases, e.g. tertiary amines, such as trimethylamine, triethylamine, tri-isopropylamine and N-methylpiperidine, pyridine, substituted pyridines, such as collidine, lutidine, and 4-dimethylaminopyridine, and also bicyclic amines. According to one aspect of the invention, the suitable base comprises at least one of sodium hydride, potassium hydroxide, potassium carbonate and triethylamine. According to another aspect, 50% (v/v) aqueous ammonia in methanol is used.

The azido group in the compounds of FIG. 3 can be reduced to an amine group by hydrogenation. Typically, hydrogenation is carried out using a noble metal catalyst, such as palladium, platinum, rhodium, or the like, optionally on carbon, as is well known in the art. Each of these reactions proceeded with very high, near quantitative, yields as judged by TLC and $^1$H NMR analysis of the products. The obtained nucleoside precursors were then sequentially protected at the 2'-hydroxyl with a trialkylsilyl containing group and at the 3'-amino group with a substituted or unsubstituted trityl group to give compound 7 (FIG. 3). After workup, the crude mixtures were treated with a base, such as 1 M solution of sodium hydroxide in pyridine/methanol/water, to remove the 5'-O-toluoyl group and afford nucleoside 8 with overall yields of 56%-60% based on starting precursors 2 (FIG. 3).

For compound 2, where the base is G or D and the 2'-O-position is protected with the acetyl group, the 2'-O-acetyl group could not be selectively removed. Therefore, in an alternative scheme, both 2'-O- and 5'-O-protecting groups were removed using a base, such as 1 M sodium hydroxide, after which a 5'-O-anisoyl group was selectively reintroduced under Mitsunobu conditions to give 4. It should be noted that the high reactivity of the 2'-hydroxyl group of the 3'-azido-2'-hydroxyl guanosine intermediate prevented selective reprotection of the 5'-hydroxyl group by either benzoyl chloride or benzoyl anhydride. The same series of steps described above was then used to convert 4 where B is G or D into the corresponding compound 8. The final step for monomer preparation involved phosphitylation of compound 8 to give the 5'-(2-cyanoethyl-N,N'-diisopropylamino)nucleoside phosphoramidite building blocks 9 (FIG. 3).

Figure 4:
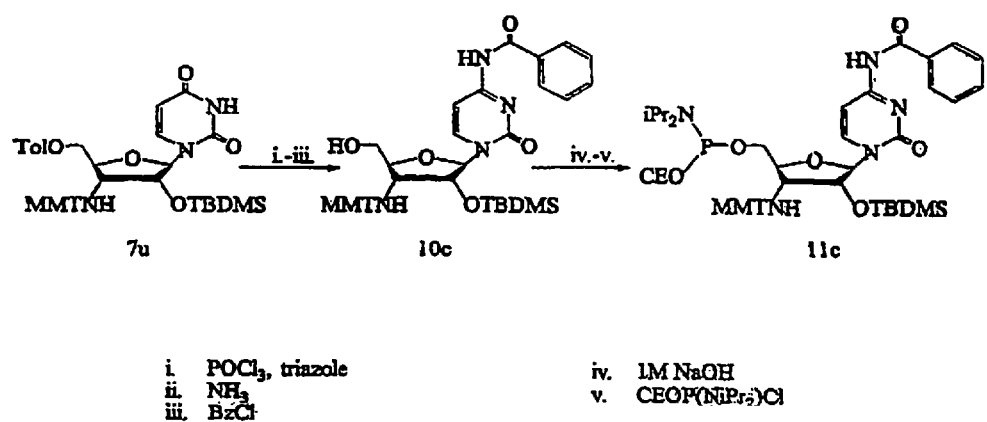
FIG. 4 shows the scheme used to prepare $N^4$-benzoyl-3'-aminocytidine analogue (10c) and 5'-(2-cyanoethyl-N,N'-diisopropylamino) phosphoramidite cytidine monomer (11c). Tol is toluoyl, MMTNH is (monomethoxytrityl)amino, OTBDMS is —O-t-butyldimethysilyl, $iPr_2N$ is diisopropylamino, and CEO is β-cyanoethyl.

In an alternative synthetic transformation, the intermediate compound 7, where B is uridine, was converted into a $N^4$-benzoyl-3'-aminocytidine analogue (10). Initially, the uridine derivative 7 was transformed into the benzoyl protected cytosine derivative according to literature procedure (FIG. 4) (Divacar, et al. (1982) *J. Chem. Soc. Perkin Trans.*, 1:1171-1176). Reaction of 7u (base is U) with triazole in the presence of phosphorus oxychloride yielded the desired 4-triazolo species, which upon treatment with ammonia generated the 4-amino-unprotected cytosine nucleoside. After workup, the crude reaction mixture was benzoylated and finally deprotected with 1 M sodium hydroxide to give 10c (FIG. 4) in 45% overall yield from the starting compound 7. Phosphitylation of 10c produced the desired 5'-(2-cyanoethyl-N,N'-diisopropylamino) phosphoramidite cytidine monomer used for oligonucleotide construction.

In an alternative method, the appropriately protected 2'-O-alkyl-3'aminonucleoside-5'-phosphoramidite building blocks 4, 6, 11, and 15, where alkyl is methyl, were prepared according to a series of chemical transformations shown in Schemes 1-3 below. A step for the preparation of these compounds was the selective methylation of the 2'-hydroxyl group in the presence of either the imino functionality of pyrimidines, or the N-7 atom of the purines. The two pyrimidine-based monomers were obtained from the known 3-azido-2'-O-acetyl-5'-O-toluoyl-3'-deoxy-β-D-ribofuranosyluracil 1. Typically, the N-3/O-4 imino nitrogen of 1 was first protected with a protecting group, such as by the reaction of methyl propyolate in the presence of dimethylaminopyridine (Scheme 1). The crude reaction product was then selectively 2'-O-deacetylated, and the resulting free 2'-hydroxyl group was then alkylated, such as by methylation using iodomethane and silver oxide. The N-3 protecting group was removed and the 3'-azido group was reduced to amine, which was then immediately protected, such as reaction with 4-monomethoxytritylchloride, to give the precursor 3. The 5'-toluoyl ester was then cleaved using an alkaline solution, followed by phosphitylation using known protocols to give the desired 2'-O-methyl uridine phosphoramidite monomer 4. The 2'-O-methyl cytosine phosphoramidite was obtained by conversion of uridine intermediate 3 into 3'-aminocytidine analogue 5.

Scheme 1

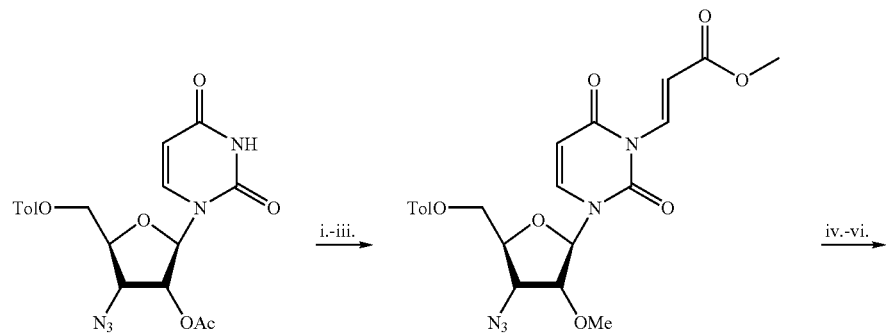

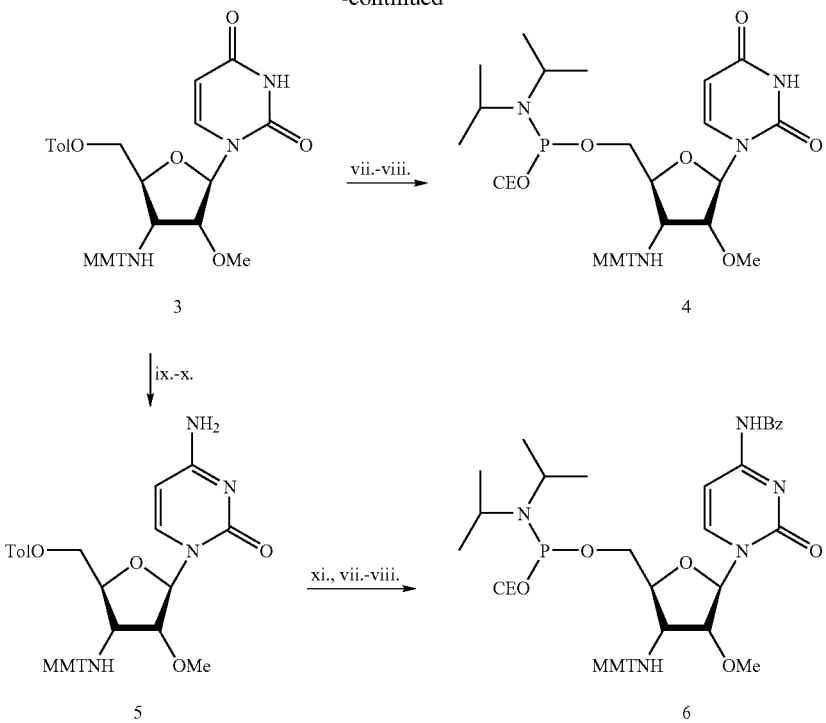

i. HC≡CCOOMe, DMAP
ii. NH₃, MeOH
iii. Ag₂O, CH₃I
iv. Piperidine
v. H₂/Pd
vi. MMTCl, NMI
vii. NaOH
viii. CEOP(NiPr₂)Cl
ix. POCl₃, Triazole
x. NH₃
xi. BzCl The synthesis of the 2'-O-alkyl adenosine analogue required the use of bulky protecting groups, primarily for exocyclic amine in order to prevent the alkylation of N-7 during methylation of the 2'-hydroxyl group (Scheme 2). 3'-Azido-2'-O-acetyl-5'-O-toluoyl-N⁶-benzoyl-3'-deoxyadenosine 7 was first deprotected, such as by reaction with NH₃/MeOH (1/1, v/v), to afford 3'-azido-3'-deoxyadenosine. Then, the 5'-hydroxyl group and the N-6 moiety were selectively re-protected with bulky protecting groups, such as the t-butyldiphenylsilyl group or the 4-monomethoxytrityl group. The combination of the two large substituents at the 5'-O and N-6 positions sterically occluded N-7, thereby allowing for the selective introduction of a methyl group at the 2'-position to produce the intermediate 8. The N-6 4-monomethoxytrityl group was then removed, such as by treatment with 3% trichloroacetic acid in an organic solvent, such as dichloromethane, followed by re-protection of N-6. The use of benzoyl chloride for the re-protection of N-6 resulted in the addition of two benzoyl groups. The second benzoyl group was subsequently removed by base treatment to produce the intermediate 9. The azide group was then reduced and the resulting 3'-amino group was protected with 4-monomethoxytrityl to form 10. Finally, the 5'-silyl protecting group was cleaved, and phosphitylation resulted in the 2'-O-methyl phosporamidite monomer 11.

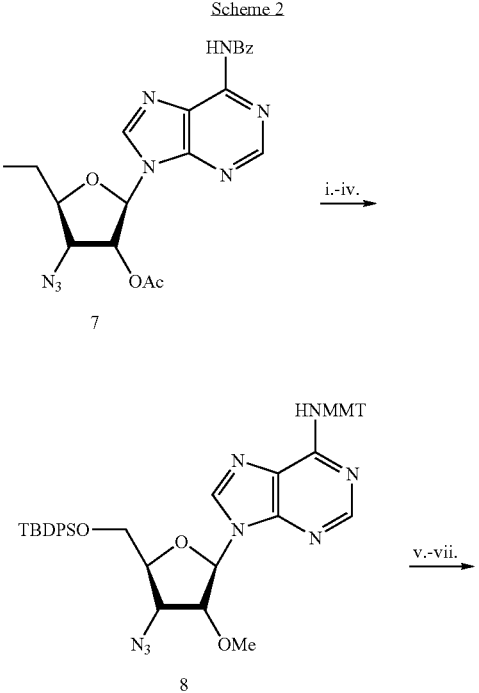

-continued

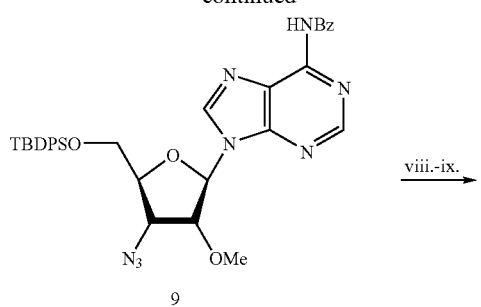
9

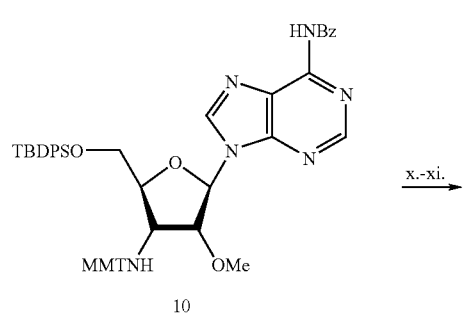
10

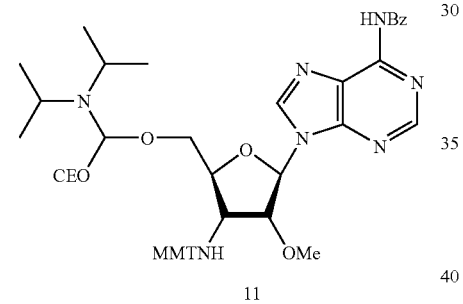
11 i. NH₃/MeOH
ii. TBDPSCl
iii. MMTCl, DMAP
iv. Ag₂O, MeI
v. TCA
vi. BzCl
vii. NaOH
viii. H₂/Pd
ix. MMTCl, NMI
x. TBAF
xi. CEOP(NiPr₂)Cl The synthesis of the guanosine-based 2'-O-alkyl phosphramidite 15 is depicted in Scheme 3. 3'-Azido-2'-O-acetyl-5'-O-toluoyl-N²-isobutryl-O⁶-diphenylcarbamoyl-3'-deoxyguanosine 12 was deblocked by treatment with a base. The 5'O- and O-6 were reprotected by reaction with t-butyldiphenylsilylchloride. The bis-silylated intermediate was then 2'-O alkylated. The O-6 silyl group was selectively deprotected to give compound 13. The N-2 group was re-protected, the 3'-azido group was reduced, and the resulting 3'-amino group was protected to yield the nucleoside 14. Finally, the 2'-O-alkyl guanosine phosphoramidite monomer 15 was obtained by removing the 5'-protecting group followed by phosphitylation of the unmasked 5'-hydroxyl.

Scheme 3

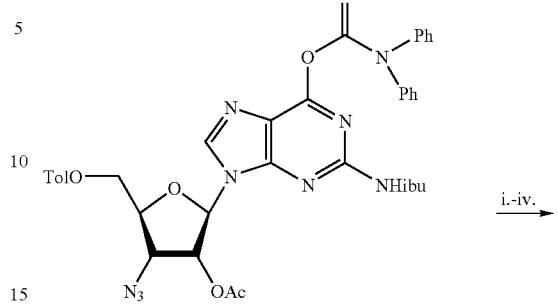
12

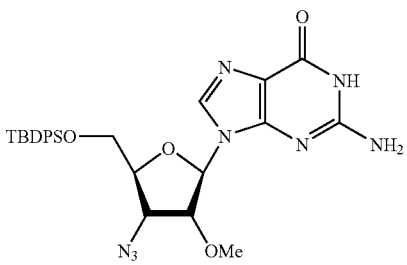
13

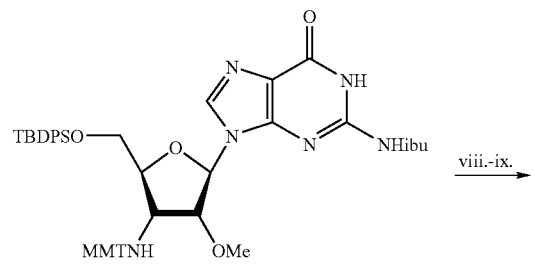
14

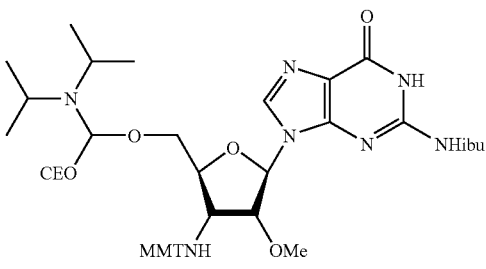
15 i. NH₃/EtOH
ii. TBDPSCl
iii. MeI, BEMP
iv. NH₃/ACN
v. iBu anhydride
vi H₂/Pd
vii. MMTCl, NMI
viii. TBAF
ix. CEOP(NiPr₂)Cl The double-stranded form of the siRNAs can be prepared by synthesizing the two single strands and adding one to the other by, e.g., annealing the strands. It is also possible to prepare a double-stranded form of the siRNA by constructing a single strand and allowing it to fold upon itself and form a hairpin duplex.

4. Design of Lipidated Riboamidate and Ribothioamidate siRNAs

The riboamidate and thioriboamidate siRNAs conjugated to lipid components are effective in RNAi applications, such as therapeutic RNAi applications, possibly more so than corresponding unconjugated riboamidates and ribothioamidates. The lipid component L is believed to function to enhance cellular uptake of the siRNA, particularly in facilitating passage through the cellular membrane. While the mechanism by which this occurs has not been fully elucidated, one possibility is that the lipid component may facilitate binding of the siRNA to the cell membrane as either a single molecule, or an aggregate (micellar) form, with subsequent internalization. However, understanding of the precise mechanism is not required for the invention to be utilized.

The lipid component can be any lipid or lipid derivative that provides enhanced cellular uptake compared to the unmodified riboamidate or ribothioamidate. Suitable non-limiting examples of lipids useful in accordance with the present invention include hydrocarbons, fats (e.g., glycerides, fatty acids and fatty acid derivatives, such as fatty amides) and sterols. Where the lipid component is a hydrocarbon, the L component can be a substituted or unsubstituted cyclic hydrocarbon or an aliphatic straight chain or branched hydrocarbon, which can be saturated or unsaturated. Suitable examples include straight chain unbranched hydrocarbons that are fully saturated or polyunsaturated. The length of the hydrocarbon chain can vary from $C_2$-$C_{30}$, but optimal results can be obtained with carbon chains that are $C_8$-$C_{22}$. Suitable non-limiting examples of saturated hydrocarbons (alkanes) are listed below:

| Systematic name | Carbon chain |
| --- | --- |
| Tetradecane | $C_{14}H_{30}$ |
| Pentadecane | $C_{15}H_{32}$ |
| Hexadecane | $C_{16}H_{34}$ |
| Heptadecane | $C_{17}H_{36}$ |
| Octadecane | $C_{18}H_{38}$ |
| Nonadecane | $C_{19}H_{40}$ |
| Eicosane | $C_{20}H_{42}$ |

Mono- and poly-unsaturated forms (alkenes and polyenes, such as alkadienes and alkatrienes) of hydrocarbons can also be selected, with compounds having one to three double bonds being suitable examples, although compounds having more double bonds can be employed. Alkynes (containing one or more triple bonds) and alkenynes (triple bond(s) and double bond(s)) can also be utilized. Examples of common mono- and poly-unsaturated hydrocarbons that can be employed include those shown in FIGS. 1M, 1L and 1O.

Substituted forms of hydrocarbons can be employed in the compounds of the invention, with substituent groups that are inert in vivo and in vitro being suitable. An example of such a suitable substituent is fluorine. Exemplary generic structures of polyfluorinated hydrocarbons include:

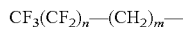

where m is at least 1, for example at least 2, and n=1-30, such as fluorotridecane: $CF_3(CF_2)_9(CH_2)_3$; and

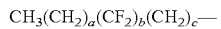

where a, b and c are independently 1-30.

Figure 1F:
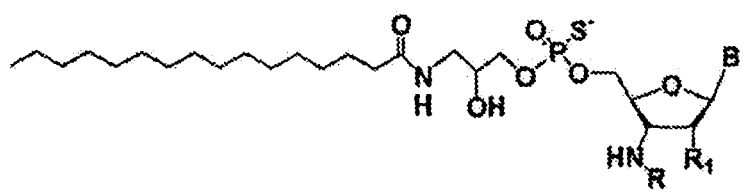
Figure 1G:
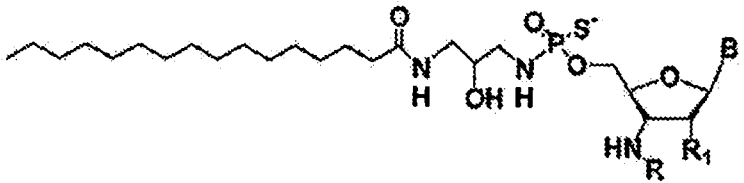
Figure 1H:
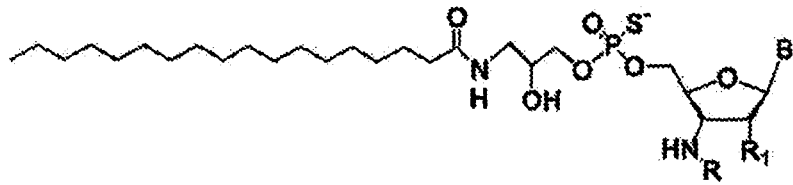
Figure 1I:
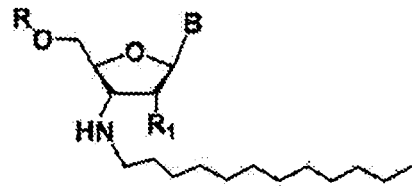
Figure 1J:
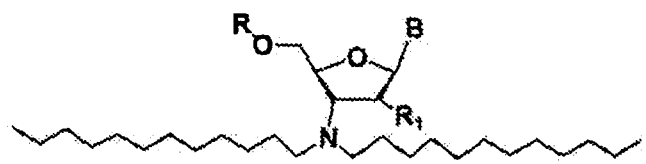
Figure 1K:
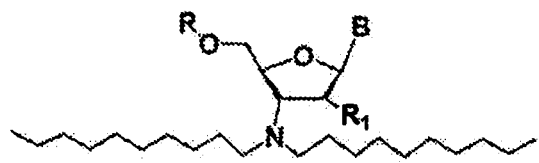
Figure 1L:
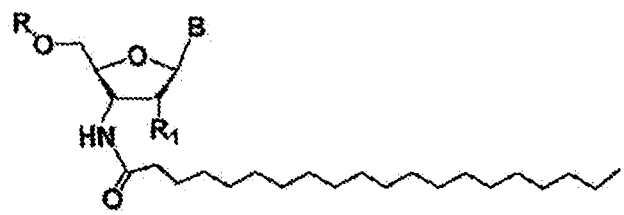
Figure 1M:
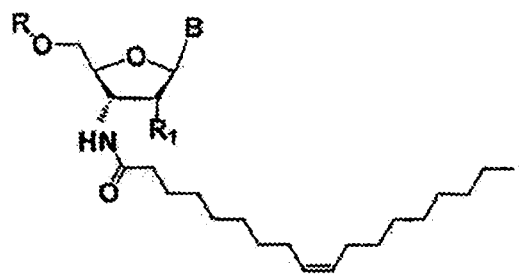
Figure 1N:
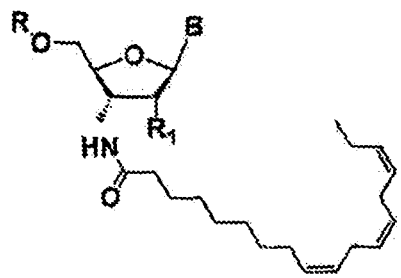
Figure 1O:
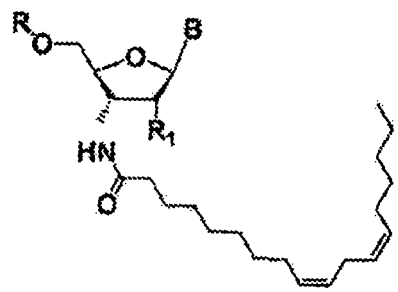
Figure 1P:
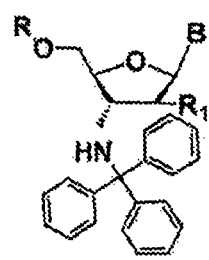
Figure 1Q:
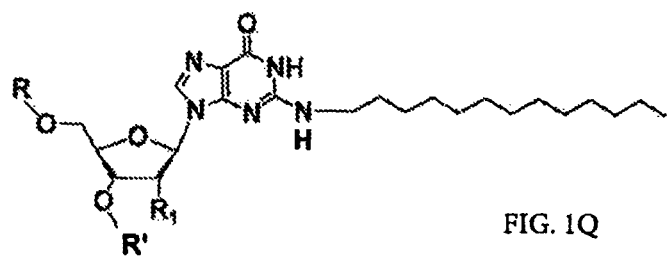
Figure 1R:
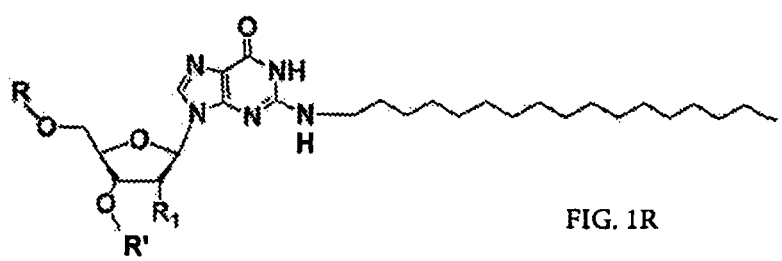
Figure 1S:
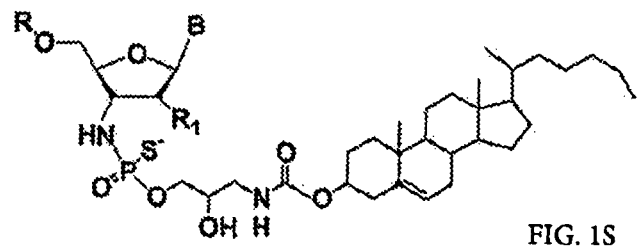
Figure 1T:
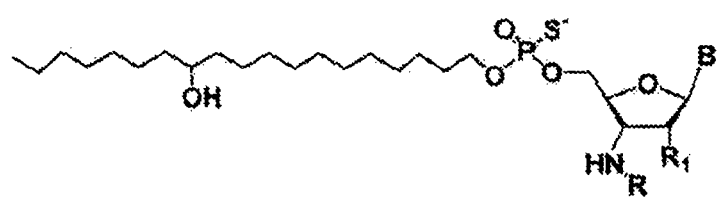
Figure 1U:
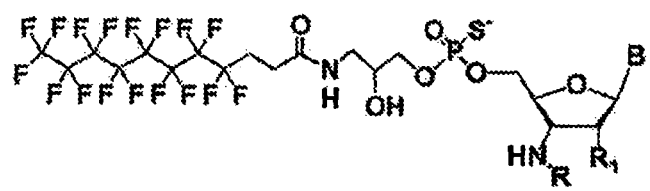
Figure 1V:
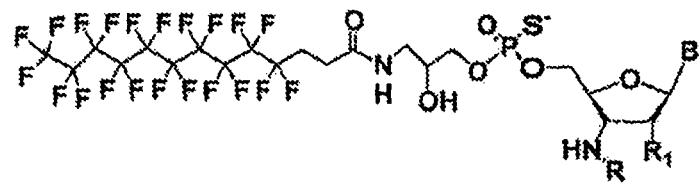
Figure 1W:
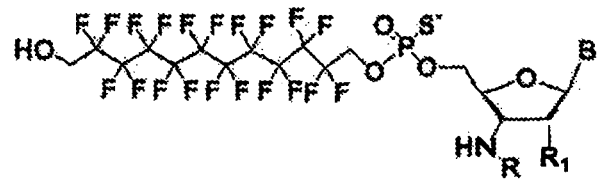
Figure 1X:
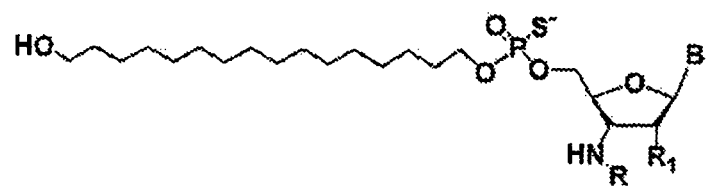
Figure 1Y:
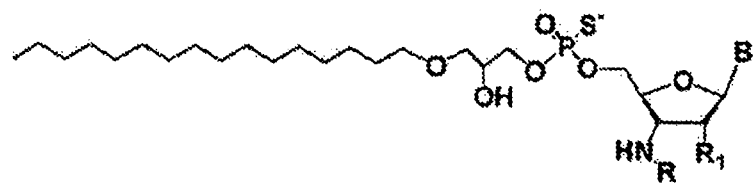

FIG. 1W shows an example of a polyfluorinated hydrocarbon conjugated to the 5' terminus of an oligonucleotide.

Other suitable lipid components include simple fatty acids and fatty acid derivatives, glycerides, and more complex lipids such as sterols, for example cholesterol. Fatty acids and their derivatives can be fully saturated or mono- or poly-unsaturated. The length of the carbon chain can vary from $C_2$-$C_{30}$, but optimal telomerase inhibition can be obtained with carbon chains that are $C_8$-$C_{22}$. Suitable non-limiting examples of saturated fatty acids are listed below:

| Systematic name | Trivial name | Carbon chain |
| --- | --- | --- |
| Tetradecanoic | myristic | 14:0 |
| Hexadecanoic | palmitic | 16:0 |
| Octadecanoic | stearic | 18:0 |
| Eicosanoic | arachidic | 20:0 |

Mono- and poly-unsaturated forms of fatty acids can also be employed, with compounds having one to three double bonds being suitable examples, although compounds having more double bonds can also be employed. Examples of common mono- and poly-unsaturated fatty acids that can be employed include:

| Systematic name | Trivial name | Carbon chain |
| --- | --- | --- |
| Cis-9-hexadecanoic | palmitoleic | 16:1 (n-7) |
| Cis-6-octadecanoic | petroselinic | 18:1 (n-12) |
| Cis-9-octadecanotc | oleic | 18:1 (n-9) |
| 9,12-octadecadienoic | linoleic | 18:2 (n-6) |
| 6,9,12-octadecatrienoic | gamma-linolenic | 18:3 (n-6) |
| 9,12,15-octadecatrienoic | alpha-linolenic | 18:3 (n-3) |
| 5,8,11,14-eicosatetraenoic | arachidonic | 20:4 (n-6) |

Fatty acids with one or more triple bonds in the carbon chain, as well as branched fatty acids can also be employed in the compounds disclosed herein. Substituted forms of fatty acids can be employed in the compounds disclosed herein. As with the hydrocarbon groups, substituent groups that are inert in vivo and in vitro are suitable examples, with fluorine being an example of such a group. Exemplary generic structures of polyfluorinated derivatives of fatty acids suitable for use in accordance with the present invention are:

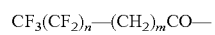

where m is at least 1, for example at least 2, and n=1-30, and

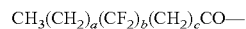

where a, b and c are independently 1-30

Examples of compounds having polyfluorinated derivatives of fatty acids are shown in FIGS. 1U and 1V.

Typically, between one and five L components (n=1-5) are covalently linked to the O component, optionally via a linker. For example, one or two L components are utilized (n=1 or 2). Where more than one L component is linked to the O component, each L component is independently selected.

It will be appreciated that compounds described as having a specified hydrocarbon as the L moiety and compounds described as having a specified fatty acid (with the same number of carbon atoms as the specified hydrocarbon) are closely related and differ in structure only in the nature of the bond that joins the L moiety to the riboamidate or ribothioamidate, which in turn is a result of the synthesis procedure used to produce the compound.

For example, and as described in more detail below, when compounds are synthesized having the L moiety conjugated to the 3'-amino terminus of a riboamidate (having phosphoramidate or thiophosphoramidate internucleoside linkages), the use of the aldehyde form of a fatty acid (a fatty aldehyde) as the starting material results in the formation of an amine linkage between the lipid chain and the riboamidate, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated L group is used broadly herein to include fatty acid derivatives, including fatty amides).

This is illustrated in the following schematics (and in FIGS. 5A and 5B), which depict the 3'-amino terminus of a phosphoramidate oligonucleotide joined to a $C_{14}$ lipid component. In schematic A, L is tetradecanoic acid (myristic acid), in which the connection between L and O groups is an amide. In schematic B, L is tetradecane, and the connection between the L and O groups is an amine.

Schematic A

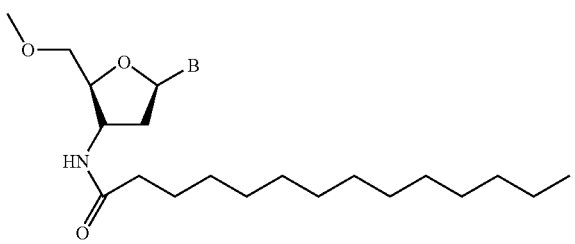

Schematic B

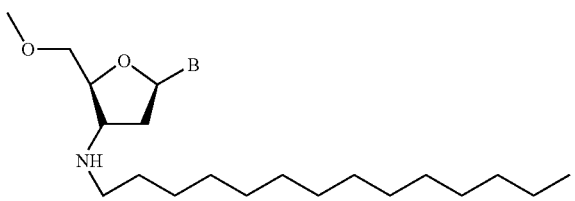

The linkage between the O and L components can be a direct linkage, or can be via an optional linker moiety, x. The linker group can serve to facilitate the chemical synthesis of the compounds (discussed in the synthesis section below). Whether or not a linker group is used to mediate the conjugation of the O and L components, there are multiple sites on the riboamidate component O to which the L component(s) can be conveniently conjugated. Suitable linkage points include the 5' and 3' termini, one or more sugar rings, the internucleoside backbone and the nucleobases of the riboamidates. Typically, the L moiety is attached to the 3' or 5' terminus of the riboamidate.

Figure 1Z:
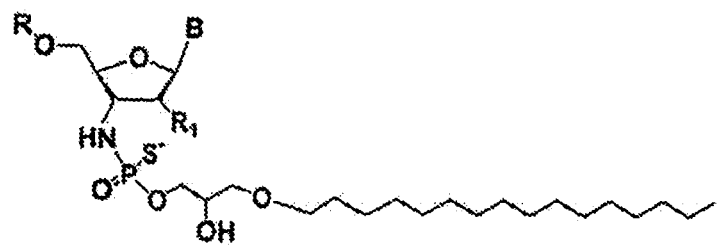
Figure 1A:
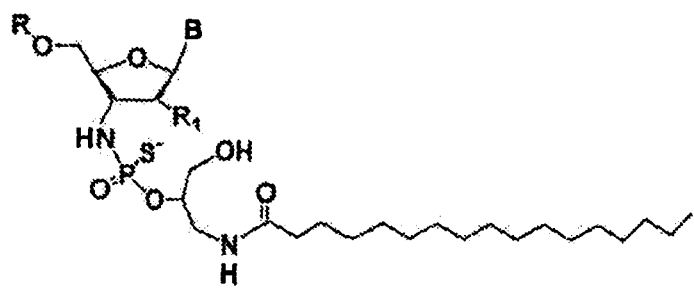
Figure 1B:
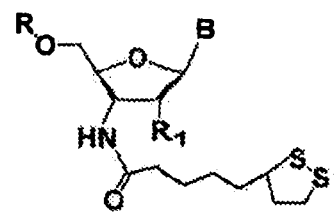
Figure 1C:
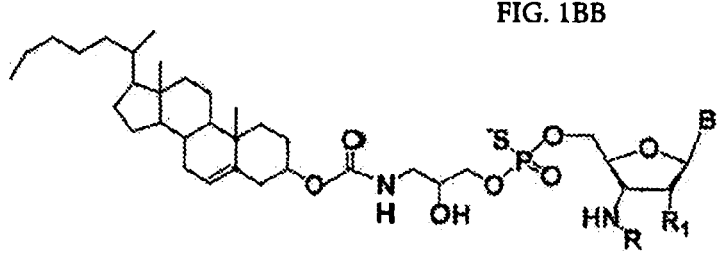

If the L component is to be attached to the 3' terminus, the attachment can be directly to the 3' substituent, which in the case of the phosphoramidate and thiophosphoramidate riboamidates is the 3'-amino group (examples are shown in FIGS. 1A-C), and in other instances, such as conventional phosphodiester oligonucleotides, is a 3-hydroxy group. Alternatively, the L moiety can be linked via a 3'-linked phosphate group (an example is shown in FIG. 1Z, in which a hexadecane hydrocarbon is linked to the 3' phosphate of a thiophosphoramidate oligonucleotide through an O-alkyl linker. If the L moiety is to be linked to the 5' terminus, it is typically attached through a 5'-linked phosphate group (see FIG. 1F which shows the use of an amino glycerol linker, and FIG. 1G which shows the use of a bis-amino glycerol linker). Attachment to a base on the O moiety can be through any suitable atom, for example to the $N^2$ amino group of guanosine (see FIGS. 1Q-R). Where n>1 such that a plurality of lipid moieties is to be attached to the O component, the individually selected L components can be attached at any suitable site(s). For example, one L group can be attached to each terminus, various L groups can be attached to the bases, or two or more L groups can be attached at one terminus (see FIGS. 1E, 1J, 1K).

In the case of single-stranded (antisense) siRNA, the lipid is suitably conjugated to the 3' end, as the presence of the 5-OH is believed to be important to the activity of the siRNA. In the case of double-stranded siRNAs, if the lipid is conjugated to the sense strand, the conjugation can be at either end. If the lipid is conjugated to the antisense strand, then it is suitably conjugated at the 3' end, or at the base. For double-stranded siRNAs, it is possible for more than one lipid to be conjugated to the siRNA.

The optional linker component x can be used to join the O and L components of the compounds. If a linker is to be employed, it is incorporated into the synthesis procedures as described in the brief description of FIG. 5, above. Examples of suitable linker groups include amino glycerol and O-alkyl glycerol-type linkers, which, respectively, can be depicted by the generic structures:

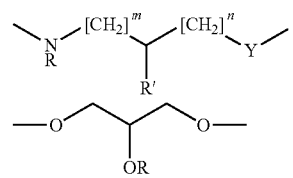

Wherein R'=H, OH, $NH_2$ or SH; Y=O, S or NR; R=H or alkyl; and n and m are independently integers between 1-18.

Specific examples of suitable linkers are the aminoglycerol linker in which R'=OH, Y=O, and m and n are each 1:

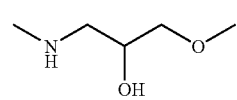

the bis-aminoglycerol linker, in which R'=OH, Y=NH, and m and n are each 1:

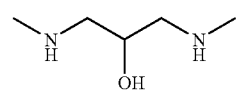

and the O-alkyl glycerol linker in which R=H:

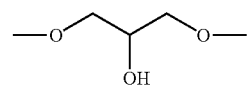

Figure 1D:
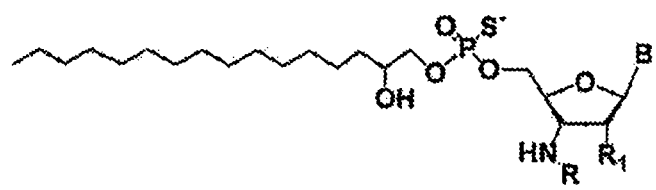

Examples of compounds disclosed herein are shown in FIG. 1. For simplicity, only one base of the component O is shown, with a generic base, B, being depicted and R indicating the attachment point for the remainder of the riboamidate. Compounds linked to the 3' terminus are illustrated with a 3'-nitrogen, consistent with thiophosphoramidate and phosphoramidate riboamidate chemistries. FIGS. 1A-1L illustrate compounds having saturated lipid groups attached to the 5' or 3' termini. FIGS. 1M-1P illustrate compounds having mono- or poly-unsaturated lipid groups. FIGS. 1Q-1R illustrate compounds having lipid groups conjugated to the riboamidate through a base (in this case, guanosine). FIGS. 1S and 1CC illustrate 3'- and 5'-conjugated cholesterol lipid moiety, respectively. FIGS. 1U and 1V illustrate 5'-conjugated poly-fluorine substituted fatty acid derivatives, and FIG. 1W illustrates a 5' conjugated polyfluorinated hydrocarbon. FIGS. 1X-Z illustrate 5' lipid moieties containing oxygen. The nomenclature used herein for each of the lipid groups illustrated is as follows:

FIG. 1A: 3'-myristoylamide
FIG. 1B: 3'-palmitoylamide
FIG. 1C: 3'-stearoylamide
FIG. 1D: 3'-palmitoylamido-propyl-thiophosphate
FIG. 1E: 3'-lysyl-bis-stearoylamide
FIG. 1F: 5'-palmitoylamido-aminoglycerol-thiophosphate
FIG. 1G: 5'-palmitoylamido-bis-aminoglycerol-thiophosphate
FIG. 1H: 5'-stearoylamido-aminoglycerol-thiophosphate
FIG. 1I: 3'-dodecyl
FIG. 1J: 3'-bis-dodecyl
FIG. 1K: 3'bis-decyl
FIG. 1L: 3'-eicosanoylamide
FIG. 1M: 3'-oleinylamide
FIG. 1N: 3'-linolenylamide
FIG. 1O: 3'-linoleylamide
FIG. 1P: 3'-trityl
FIG. 1Q: $N^2$-tetradecyl guanosine
FIG. 1R: $N^2$-octadecyl-guanosine
FIG. 1S: 3'-cholesterylamido-aminoglycerol-thiophosphate
FIG. 1T: 5'-(12-OH)-stearoyl-thiophosphate
FIG. 1U: 5'-C11-Teflon-thiophosphate
FIG. 1V: 5'-C13-Teflon-thiophosphate
FIG. 1W: 5'-OH-C10-Teflon-thiophosphate
FIG. 1X: 5'-OH-palmityl-thiophosphate
FIG. 1Y: 5'-batyl-thiophosphate
FIG. 1Z: 3'-batyl-thiophosphate
FIG. 1AA: 3'-palmitoylamido-aminoglycerol-thiophosphate
FIG. 1BB: 3'-thioctylamide
FIG. 1CC: 5'-cholesterylamido-aminoglycerol-thiophosphate
FIG. 1DD: 5'-(2-OH)-hexadecanol-thiophosphate 5. Synthesis of Lipidated Riboamidate and Ribothioamidate siRNAs A variety of synthetic approaches can be used to conjugate the lipid moiety L to the riboamidate, depending on the nature of the linkage selected, including the approaches described in Mishra et al., (1995) Biochemica et Biophysica Acta, 1264: 229-237, Shea et al., (1990) Nucleic Acids Res. 18:3777-3783, and Rump et al., (1998) Bioconj. Chem. 9:341-349. The synthesis of compounds in which the lipid moiety is conjugated at the 5' or 3' terminus of the riboamidate can be achieved through use of suitable functional groups at the appropriate terminus, most typically an amino group, which can be reacted with carboxylic acids, acid chlorides, anhydrides and active esters. Thiol groups are also suitable as functional groups (see Kupihar et al., (2001) Bioorganic and Medicinal Chemistry 9:1241-1247). Both amino- and thiol-modifiers of different chain lengths are commercially available for riboamidate synthesis.

Riboamidates having N3'→P5' phosphoramidate and N3'→P5' thiophosphoramidate linkages contain 3'-amine groups (rather than 3'-hydroxy found in most conventional oligonucleotide chemistries), and hence these riboamidates provide a unique opportunity for conjugating lipid groups to the 3'-end of the riboamidate.

Various approaches can be used to attach lipid groups to the termini of riboamidates with the N3'→P5' phosphoramidate and N3→P5' thiophosphoramidate chemistries. Examples of synthetic schemes for producing the conjugated compounds are shown in FIG. 5.

For attachment to the 3' terminus, the conjugated compounds can be synthesized by reacting the free 3'-amino group of the fully protected solid support bound riboamidates with the corresponding acid anhydride followed by deprotection with ammonia and purification. Alternatively, coupling of carboxylic acids of lipids to the free 3'-amino group of the support bound riboamidate using coupling agents, such as carbodiimides, HBTU or 2-chloro-1-methylpyridinium iodide can be used to conjugate the lipid groups. These two methods will form an amide bond between the lipid and the riboamidate. Lipids can also be attached to the riboamidate chain using a phosphoramidite derivative of the lipid coupled to the riboamidate during chain elongation. This approach yields a phosphoramidate or thiophosphoramidate linkage connecting the lipid and the riboamidate (exemplified by propyl-palmitoyl and 2-hydroxy-propyl-palmitoyl compounds). Still another approach involves reaction of the free 3'-amino group of the fully protected support bound riboamidate with a suitable lipid aldehyde, followed by reduction with sodium cyanoborohydride, which produces an amine linkage.

For attachment to the 5' terminus of, e.g., the sense strand of a double-stranded siRNA, the riboamidate can be synthesized using a modified, lipid-containing solid support, followed by synthesis of the riboamidate in the 5- to 3' direction as generally described in Pongracz & Gryaznov (1999). An example of the modified support is provided in Schematic C below. In the instance where n=14, the fatty acid is palmitic acid: reaction of 3-amino-1,2-propanediol with palmitoyl chloride, followed by dimethoxytritylation and succinylation provided the intermediate used for coupling to the solid support. R is long chain alkyl amine controlled pore glass.

Schematic C

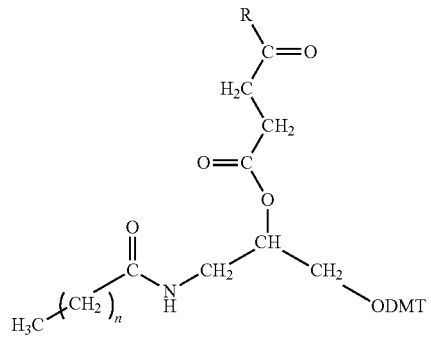

6. Formulation of Invention Compounds

For therapeutic application, a compound according to the present invention is formulated in a therapeutically effective amount with a pharmaceutically acceptable carrier. One or more such compounds (for example, having different L or O components) can be included in any given formulation. The pharmaceutical carrier can be solid or liquid. Liquid carriers can be used in the preparation of solutions, emulsions, suspensions, and pressurized compositions. The compounds are dissolved or suspended in a pharmaceutically acceptable liquid excipient. Suitable examples of liquid carriers for parenteral administration of the riboamidate preparations include water (which can contain additives, e.g., cellulose derivatives, for example sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers, and osmolarity regulators.

For parenteral administration of the compounds, the carrier can also be an oily ester, such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The riboamidates can also be administered intravascularly or via a vascular stent.

The liquid carrier for pressurized compositions can be a halogenated hydrocarbon or other pharmaceutically acceptable propellant. Such pressurized compositions can also be lipid encapsulated for delivery via inhalation. For administration by intranasal or intrabronchial inhalation or insufflation, the riboamidates can be formulated into an aqueous or partially aqueous solution, which can then be utilized in the form of an aerosol.

The compounds can be administered topically as a solution, cream, or lotion, by formulation with pharmaceutically acceptable vehicles containing the active compound.

The pharmaceutical compositions can be orally administered in any acceptable dosage including, but not limited to, formulations in capsules, tablets, powders or granules, and as suspensions or solutions in water or non-aqueous media. Pharmaceutical compositions and/or formulations comprising the riboamidates as disclosed herein can include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents can also be added.

While the compounds have superior characteristics for cellular and tissue penetration, they can be formulated to provide even greater benefit, for example, in liposome carriers. The use of liposomes to facilitate cellular uptake is described, for example, in U.S. Pat. No. 4,897,355 and U.S. Pat. No. 4,394,448. Numerous publications describe the formulation and preparation of liposomes. The compounds can also be formulated by mixing with additional penetration enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.).

Complex formulations comprising one or more penetration enhancing agents can be used. For example, bile salts can be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the riboamidates can also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents, such as diclofenac sodium, indomethacin, and phenylbutazone.

Thus, in another aspect of the invention, there is provided a method of formulating a pharmaceutical composition, the method comprising providing a compound as described herein, and combining the compound with a pharmaceutically acceptable excipient. The compound can be provided at pharmaceutical purity, as defined below. The method can further comprise adding to the compound, either before or after the addition of the excipient, a penetration enhancing agent.

The pharmaceutical composition will typically comply with pharmaceutical purity standards. For use as an active ingredient in a pharmaceutical preparation, a compound such as those described in the present invention is generally purified away from other reactive or potentially immunogenic components present in the mixture in which they are prepared. Typically, to achieve pharmaceutical purity where a nucleic acid-based compound is the active ingredient, the active ingredient is provided in at least about 50% homogeneity, for example 60%, 70%, 80% or 90% homogeneity, as determined by functional assay, chromatography, or gel electrophoresis. The active ingredient is then compounded into a medicament in accordance with generally accepted procedures for the preparation of pharmaceutical preparations. Thus, in accordance with the present invention, providing the compounds at pharmaceutical purity requires that the compound be provided at at least about 50% homogeneity, for example at least 80% or 90% homogeneity.

The pharmaceutical composition will also typically be aliquoted and packaged in either single dose or multi-dose units. The dosage requirements for treatment with the riboamidate compound vary with the particular compositions employed, the route of administration, the severity of the symptoms presented, the form of the compound and the particular subject being treated.

Pharmaceutical compositions as disclosed herein can be administered to a subject in a formulation and in an amount effective to achieve a clinically desirable result. The amount of compound per dose and the number of doses required to achieve such effects will vary depending on many factors including the disease indication, characteristics of the patient being treated and the mode of administration. Typically, the formulation and route of administration will provide a local concentration at the disease site of between 1 µM and 1 nM of the compound.

In general, the compounds are administered at a concentration that affords effective results without causing any harmful or deleterious side effects. Such a concentration can be achieved by administration of either a single unit dose, or by the administration of the dose divided into convenient subunits at suitable intervals throughout the day.

What is claimed is:

1. An isolated small double stranded interfering RNA (siRNA)
   wherein one strand is complementary to a target nucleic acid sequence and both strands are from 19 to 25 nucleotides in length, and
   wherein at least one strand of the RNA comprises an oligonucleotide wherein all of the nucleosides are of the formula:

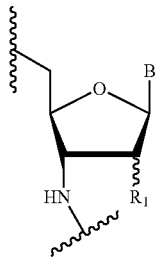

wherein $R_1$ is chosen from fluorine and $OR_2$, $R_2$ is chosen from hydrogen and lower alkyl, and B is chosen from purines, pyrimidines, and analogs thereof, and wherein all of the internucleoside linkages in the oligonucleotide are ribo N3'→P5' thiophosphoramidate linkages of the formula 3'-[—NH—P(=O)(—XR)—O-]-5', wherein X is S and R is selected from hydrogen, alkyl and aryl.

2. The small interfering RNA according to claim 1, wherein the RNA further comprises at least one covalently conjugated lipid moiety.

3. The small interfering RNA according to claim 2, wherein the lipid moiety is covalently conjugated to the 5' or 3' terminus of at least one strand of the double-stranded RNA, and the lipid moiety is chosen from fatty acids, sterols and hydrocarbons.

4. The small interfering RNA according to claim 2, wherein at least one strand comprises the structure:

wherein
O is an oligonucleotide of formula:

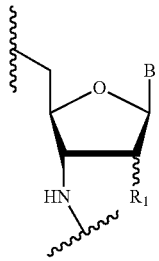

wherein $R_1$ is chosen from fluorine and $OR_2$, $R_2$ is chosen from hydrogen and lower alkyl, B is chosen from purines, pyrimidines, and analogs thereof, and wherein all of the internucleoside linkages in the oligonucleotide are ribo N3'→P5' thiophosphoramidate linkages of the formula 3'-[—NH—P(=O)(—XR)—O-]-5', wherein X is S and R is selected from hydrogen, alkyl and aryl, and further wherein the oligonucleotide comprises a sequence of 19 to 25 bases, and said sequence is at least partially complementary to a selected target sequence;
   L is a lipid moiety;
   x is an optional linker; and
   n is an integer ranging from 1 to 5, wherein if n>1, each additional (x-L) component may be, independently, the same or different.

5. The small interfering RNA according to claim 4, wherein L is a lipid chosen from substituted and unsubstituted fatty acids and sterols; or wherein L is chosen from substituted and unsubstituted hydrocarbons.

6. The small interfering RNA according to claim 5, wherein L is chosen from fatty acids substituted with at least one fluorine; or wherein L is chosen from hydrocarbons substituted with at least one fluorine.

7. The small interfering RNA according to claim 1, wherein at least 60% of the nucleobases in the oligonucleotide are ribonucleobases.

8. A method for effecting the post-transcriptional silencing of at least one gene, comprising administering to a mammal in need of such post-transcriptional silencing at least one small interfering RNA according to claim 1.

9. The method of claim 8, wherein the small interfering RNA further comprises at least one covalently conjugated lipid moiety.

10. The method of claim 8, wherein the at least one gene encodes at least one mRNA chosen from cellular mRNAs and viral mRNAs; or wherein the at least one gene is an oncogene; or wherein the at least one gene is a viral gene.

11. A method for effecting the post-transcriptional silencing of at least one gene, comprising administering to a mammal in need of such post-transcriptional silencing at least one small interfering RNA according to claim 4.

12. The method according to claim 11, wherein the at least one gene encodes at least one mRNA chosen from cellular mRNAs and viral mRNAs; or wherein the at least one gene is an oncogene; or wherein the at least one gene is a viral gene.

13. A small interfering RNA as recited in claim 1 wherein said target nucleic acid sequence is a human immunodeficiency virus (HIV) gene, such that said siRNA modulates expression of said HIV gene.

14. The small interfering RNA according to claim 4, wherein n=1 and the x-L component is covalently conjugated to the 5' terminus of the oligonucleotide O.

15. The small interfering RNA to claim 4, wherein n=1 and the (x-L) component is covalently conjugated to the 3' terminus of the oligonucleotide O.

16. The small interfering RNA according to claim 4, wherein n=2, one (x-L) component is covalently conjugated to the 5' terminus and one independently chosen (x-L) component is covalently conjugated to the 3' terminus.

17. A composition comprising at least one small interfering RNA according to claim 1 in an amount effective to modulate the expression of at least one gene.

* * * * *